United States Patent
Huising et al.

(10) Patent No.: US 9,314,506 B2
(45) Date of Patent: Apr. 19, 2016

(54) METHODS FOR INCREASING INSULIN SECRETION BY CO-STIMULATION OF CORTICOTROPIN-RELEASING FACTOR RECEPTORS

(71) Applicant: Research Development Foundation, Carson City, NV (US)

(72) Inventors: Mark Huising, San Diego, CA (US); Masahito Matsumoto, Hidaka (JP); Wylie Vale

(73) Assignee: Research Development Foundation, Carson City, NV (US)

(*) Notice: Subject to any disclaimer, the term of this patent is extended or adjusted under 35 U.S.C. 154(b) by 0 days.

(21) Appl. No.: 13/659,437

(22) Filed: Oct. 24, 2012

(65) Prior Publication Data

US 2013/0109621 A1 May 2, 2013

Related U.S. Application Data

(60) Provisional application No. 61/550,754, filed on Oct. 24, 2011.

(51) Int. Cl.
*A61K 38/22* (2006.01)
*C12N 5/071* (2010.01)

(52) U.S. Cl.
CPC ............ *A61K 38/2228* (2013.01); *A61K 38/22* (2013.01); *C12N 5/0676* (2013.01); *C12N 2501/998* (2013.01)

(58) Field of Classification Search
None
See application file for complete search history.

(56) References Cited

U.S. PATENT DOCUMENTS

| | | | | |
|---|---|---|---|---|
| 7,875,453 | B2 | 1/2011 | Collins | 435/377 |
| 7,932,084 | B2 | 4/2011 | Katz et al. | 435/325 |
| 2002/0082409 | A1 | 6/2002 | Hsu et al. | 536/23.5 |
| 2003/0148956 | A1 | 8/2003 | Isfort et al. | 514/10.8 |
| 2006/0057124 | A1 | 3/2006 | Shim et al. | 424/93.7 |
| 2009/0149629 | A1 | 6/2009 | Rivier et al. | 530/317 |
| 2010/0081200 | A1 | 4/2010 | Rajala et al. | 435/377 |
| 2010/0143313 | A1 | 6/2010 | Yarmush et al. | 424/93.7 |
| 2010/0317104 | A1 | 12/2010 | Elefanty et al. | 435/366 |

FOREIGN PATENT DOCUMENTS

| | | |
|---|---|---|
| WO | WO 2007/007982 | 1/2007 |
| WO | WO 2009/043521 | 4/2009 |
| WO | WO 2009/055818 | 4/2009 |
| WO | WO 2009/117098 | 9/2009 |
| WO | WO 2010/093655 | 8/2010 |

OTHER PUBLICATIONS

Biller. Latest Neuroendocrine Newsletter. 19(1):2012.*
Fekete et al. Front Neuroendocrinol. 28(1);1-27:2007.*
Huising et al. PNAS. 107(2);912-917:2010.*
Davis et al. J Clin Endocrin Metab. 89(3);1402-1409:2004.*
Mazur et al. J Med Chem. 47;3450-3454:2004.*
Bale and Vale, "CRF and CRF receptors: role in stress responsivity and other behaviors," *Annu. Rev. Pharmacol. Toxicol.*, 44:525-57, 2004.
Cheng, et al., "Cardiomyocyte-restricted peroxisome proliferator-activated receptor-delta deletion perturbs myocardial fatty acid oxidation and leads to cardiomyopathy," *Nat. Med.*, 10:1245-50, 2004.
Hauger, et al., "Corticotropin releasing factor (CRF) receptor signaling in the central nervous system: new molecular targets," *CNS Neurol. Disord. Drug Targets*, 5:453-79, 2006.
Hauger, et al., "International Union of Pharmacology. XXXVI. Current status of the nomenclature for receptors for corticotropin-releasing factor and their ligands," *Pharmacol Rev.*, 55:21-6, 2003.
He, et al., "Human embryonic stem cells develop into multiple types of cardiac myocytes: action potential characterization," *Circ. Res.*, 93:32-39, 2003.
Hillhouse and Grammatopoulos, "The molecular mechanisms underlying the regulation of the biological activity of corticotropin-releasing hormone receptors: implications for physiology and pathophysiology," *Endocr. Rev.*, 27:260-86, 2006.
Huising, et al., "CRFR1 is expressed on pancreatic beta cells, promotes beta cell proliferation, and potentiates insulin secretion in a glucose-dependent manner," *Proc. Natl. Acad. Sci. USA*, 107:912-7, 2010.
Huising et al., "Glucocorticoids differentially regulate the expression of CRF1 and CRFR2α in MIN6 insulinoma cells and rodent islets," *Endocrinology*, 152:138-150, 2011.
International Search Report and Written Opinion, issued in PCT/US2012/061593, dated Jan. 30, 2013.
Kuperman and Chen, "Urocortins: emerging metabolic and energy homeostasis perspectives," *Trends Endocrinol. Metab.*, 19:122-9, 2008.
Lehman and Kelly, "Transcriptional activation of energy metabolic switches in the developing and hypertrophied heart," *Clin. Exp. Pharmacol. Physiol.*, 29:339-45, 2002.
Li, et al., "Urocortin 1 improves renal function in rats with streptozotocin-induced diabetes by inhibiting overproduction of TGF-beta 1 and VEGF," *Br. J. Pharmacol.*, 157:994-1003, 2009.
Li, et al, "Urocortin 3 regulates glucose-stimulated insulin secretion and energy homeostasis," *Proc. Natl. Acad. Sci. USA*, 104:4206-11, 2007.
Li, et al., "Urocortin ameliorates diabetic nephropathy in obese db/db mice," *Br. J. Pharmacol.*, 154:1025-34, 2008.
Li, et al., "Urocortin III is expressed in pancreatic beta-cells and stimulates insulin and glucagon secretion," *Endocrinology*, 144:3216-24, 2003.

(Continued)

*Primary Examiner* — Karlheinz R Skowronek
*Assistant Examiner* — Schuyler Milton
(74) *Attorney, Agent, or Firm* — Parker Highlander PLLC

(57) ABSTRACT

Methods and compositions are provided for stimulating insulin production, increasing beta cell mass, or decreasing beta cell loss in a subject. For example, methods of the embodiments can comprise administration of a corticotropin-releasing factor (CRF)$_1$ receptor agonist and a CRF$_2$ receptor agonist. Also provided are pharmaceutical compositions comprising a selective CRF$_1$ receptor agonist and a selective CRF$_2$ receptor agonist.

8 Claims, 5 Drawing Sheets

(56) References Cited

OTHER PUBLICATIONS

Lopaschuk and Jaswal, "Energy metabolic phenotype of the cardiomyocyte during development, differentiation, and postnatal maturation," *J. Cardiovasc. Pharmacol.*, 56:130-40.

O'Carroll, et al., "Vasopressin potentiates corticotropin-releasing hormone-induced insulin release from mouse pancreatic beta-cells," *J. Endocrinol.*, 197:231-9, 2008.

Perrin and Vale, "Corticotropin releasing factor receptors and their ligand family," *Ann. N.Y. Acad. Sci.*, 885:312-28, 1999.

Rivier, et al., "Stressin1-A, a potent corticotropin releasing factor receptor 1 (CRF1)-selective peptide agonist," *J. Med. Chem.*, 50:1668-74, 2007.

Sharma, et al., "Murine embryonic stem cell-derived hepatic progenitor cells engraft in recipient livers with limited capacity of liver tissue formation," *Cell Transplant.*, 17:313-23, 2008.

Donaldson et al., "Cloning and characterization of human urocortin", *Endocrinology*, 137(5):2167-2170, 1996.

Vaughan et al., "Urocortin, a mammalian neuropeptide related to fish urotensin I and to corticotropin-releasing factor", *Nature*, 378:287-292, 1995.

* cited by examiner

```
Homo        mrqagraallaallllvqlcpgssqrspe----aagvqdpslrwspgarnqgg-garall
Bos         mktagraallaallllaqlrpgssqwspeeeaaaagvrdprlrwspgtrnhgg-garall
Mus         miqrgratllvallllaqlrpessqwspa-aaaatgvqdpnlrwspgvrnqgg-gvrall
Sus         mrpaglaallaallllaqlrpgssqwsp--eaavagvqdpslrwsprtqkhggsgarall
Cricetulus  mrqrgraallvallllaqlrpgssqwspa-teaatgvqdpnlrwspgarnqgg-garall
Rattus      mrqrgratllvallllvqlrpessqwspa-aaaanvvqdpnlrwnpgvrnqgg-gvrall Homo        lllaerfp-rragpgrlglgtagerprrdnpslsidltfhllrtllelartqsqreraeq
Bos         lllaerfprrraeqgrwgsgtagerprrddpplsidltfhllrtllelartqsqreraeq
Mus         lllaerfp-rra-----gsepagerqrrddpplsidltfhllrtllelartqsqreraeq
Sus         lllaerfp-rragqgrwgsgaaserprrddpplsidltfhllrtllelartqsqreraeq
Cricetulus  lllaerfp-rra-----gsgtagerqrrddpplsidltfhllrtllelartqsqreraeq
Rattus      lllaerfp-rra-----gsepagerqrrddpplsidltfhllrtllelartqsqreraeq Homo        nriifdsvgk
Bos         nriifdsvgk
Mus         nriifdsvgk
Sus         nriifdsvgk
Cricetulus  nriilnavgk
Rattus      nriifdsvgk
```

FIG. 2

```
Homo   Ucn3    mlmpvhfllllllllgg----prtglphkfykakpifsclntalseaekgqwedasllsk
Bos    Ucn3    mlipiyfllvlllllga----pqvglsqrspkagsspsclhtalreaeksqrkdtsllik
Mus    Ucn3    mlmptyfllpllllllgg----prtslshkfyntgpvfsclntalsevkknkledvpllsk
Rattus Ucn3    mlmptyfllllllllgg----prtslshkfynagpvfsclntalsevkknkledvpvlsk
Homo   Ucn2    -mtrcallllmvlmlgrvlvvpvtpip---------------------------------
Bos    Ucn2    -mtrcalvllmvlklgrtllvpatpip---------------------------------
Mus    Ucn2    mmtrwalvvfvvlmldrilfvpgtpip---------------------------------
Rattus Ucn2    mmtrwalvvfmvlmldr---vpgtpip---------------------------------

Homo   Ucn3    rsfhylrsrdassgeeeegke---kktfpisgarggarg---tryryvsqaqprgkprqd
Bos    Ucn3    rtfpalprgdpedqegqeeedte-krtfpgsvgggggggagstrykypsqaqfqgrpsqd
Mus    Ucn3    ksfghlptqdpsgeeddnqthlqikrtfsgaaggngags---tryryqsqaqhkgklypd
Rattus Ucn3    knfgylptqdpsgeeedeqkhiknkrtfsdavggnggrs---iryryqsqapkgklypd
Homo   Ucn2    -tfqlrpqnsp-------------qttprpaasespsa---------aptwpwaaqshc
Bos    Ucn2    -qfqllpqnfp-------------qatacpvtsespsg---------sttapsaawgrp
Mus    Ucn2    -tfqllpqnsl-------------ettpssvtsesssg---------tttgpsaswsns
Rattus Ucn2    -tfqllpqnyp-------------ettpssvssespsd---------tttgpsaswsns Homo   Ucn3    taksphrtkftlsldvptnimnllfniakaknlraqaaanahlmaqigrkk
Bos    Ucn3    kaksdrrtkvtlsldvptnimnilfniakaknlrakaaanahlmaqigkkk
Mus    Ucn3    kpksdrgtkftlsldvptnimnilfnidkaknlrakaaanaqlmaqigkkk
Rattus Ucn3    kvkndrgtkftlsldvptnimnilfnidkaknlrakaaanaqlmaqigkkk
Homo   Ucn2    sptrhpgsrivlsldvpigllqilleqararaareqattnarilarvghc-
Bos    Ucn2    spdphpgpritlsldvplgllqilleqararavreqaaanarilahvghr-
Mus    Ucn2    kaspyldtrvilsldvpigllrilleqarykaarnqaatnaqilahvgrr-
Rattus Ucn2    kaspyldtrvilsldvpigllrilleqarnkaarnqaatnaqilarvgrr-
```

FIG. 3

```
Homo     mrlpllvsagvllvallpcppcrallsrgpvpgarqapqhpqpldffqpppqseqpqqpq
Bos      mrlpllvsvgvllvallpsppcrallsrgpipgarqasqhpqplxffqp---ppqpqepq
Mus      mrlrllvsagmllvalssclpcrallsrgsvpra---prapqplnflqp----eqpqqpq
Sus      mrlpllvsagvllvallpcppcrallsrgpvlgarqapqhpqaldflqp---qqqpqqpq
Rattus   mrlrllvsagmllvalspclpcrallsrgsvsga---prapqplnflqp----eqpqqpq
Ovis     mrlpllvsvgvllvallpsppcrallsrgpipgarqasqhpqplsffqp---lpqpqepq Homo     arpvllrmgeeyflrlgnlnkspaaplspassllaggsgsrpspeqatanffrvllqqll
Bos      alptllrvgeeyflrlgnldetraaplspaasplasrsssrlspdkvaanffrallq---
Mus      --pvlirmgeeyflrlgnlnrspaarlspnstpltagrgsrpshdqaaanffrvllqqlq
Sus      prpvllrmgeeyflrlgnlnkspaaplspasspltgssgnr--pdevaanffrallqqlp
Rattus   --pilirmgeeyflrlgnlnrspaarlspnstpltagrgsrpshdqaaanffrvllqqlq
Ovis     alptllrvgeeyflrlgnldetraaplspaasplasrsssrlspdkvaanffrallq---

Homo     lprrsldspaalaergarnalgghqeap-ererrseeppisldltfhllrevlemaraeq
Bos      -prrpfdspagpaergtenalgsrqeapaarkrrsqeppisldltfhllrevlemtkadq
Mus      mpqrsldsraepaergaedalgghqgal-ererrseeppisldltfhllrevlemaraeq
Sus      lprrpldspsgpaergaenalssrqeap-ererrseeppisldltfhllrevlemaraeq
Rattus   mpqrpldsstelaergaedalgghqgal-ererrseeppisldltfhllrevlemaraeq
Ovis     -prrpldspagpakrgtenalgsrqeapaarkrrsqeppisldltfhllrevlemtkadq Homo     laqqahsnrklmeiigk
Bos      laqqahxnrklldiagk
Mus      laqqahsnrklmeiigk
Sus      laqqahsnrklmeiigk
Rattus   laqqahsnrklmeiigk
Ovis     laqqahsnrklldiagk
```

FIG. 4

SEQUENCE LISTING

<160> NUMBER OF SEQ ID NOS: 41

<210> SEQ ID NO 1
<211> LENGTH: 124
<212> TYPE: PRT
<213> ORGANISM: Homo sapiens

<400> SEQUENCE: 1

Met Arg Gln Ala Gly Arg Ala Ala Leu Leu Ala Ala Leu Leu Leu Leu
1               5                   10                  15

Val Gln Leu Cys Pro Gly Ser Ser Gln Arg Ser Pro Glu Ala Ala Gly
            20                  25                  30

Val Gln Asp Pro Ser Leu Arg Trp Ser Pro Gly Ala Arg Asn Gln Gly
        35                  40                  45

Gly Gly Ala Arg Ala Leu Leu Leu Leu Ala Glu Arg Phe Pro Arg
    50                  55                  60

Arg Ala Gly Pro Gly Arg Leu Gly Leu Gly Thr Ala Gly Glu Arg Pro
65                  70                  75                  80

Arg Arg Asp Asn Pro Ser Leu Ser Ile Asp Leu Thr Phe His Leu Leu
                85                  90                  95

Arg Thr Leu Leu Glu Leu Ala Arg Thr Gln Ser Gln Arg Glu Arg Ala

```
                100                 105                 110

Glu Gln Asn Arg Ile Ile Phe Asp Ser Val Gly Lys
            115                 120

<210> SEQ ID NO 2
<211> LENGTH: 129
<212> TYPE: PRT
<213> ORGANISM: Bos taurus

<400> SEQUENCE: 2

Met Lys Thr Ala Gly Arg Ala Ala Leu Leu Ala Ala Leu Leu Leu Leu
1               5                   10                  15

Ala Gln Leu Arg Pro Gly Ser Ser Gln Trp Ser Pro Glu Glu Glu Ala
            20                  25                  30

Ala Ala Ala Gly Val Arg Asp Pro Arg Leu Arg Trp Ser Pro Gly Thr
        35                  40                  45

Arg Asn His Gly Gly Gly Ala Arg Ala Leu Leu Leu Leu Ala Glu
    50                  55                  60

Arg Phe Pro Arg Arg Ala Glu Gln Gly Arg Trp Gly Ser Gly Thr
65                  70                  75                  80

Ala Gly Glu Arg Pro Arg Arg Asp Asp Pro Pro Leu Ser Ile Asp Leu
                85                  90                  95

Thr Phe His Leu Leu Arg Thr Leu Leu Glu Leu Ala Arg Thr Gln Ser
            100                 105                 110

Gln Arg Glu Arg Ala Glu Gln Asn Arg Ile Ile Phe Asp Ser Val Gly
        115                 120                 125

Lys

<210> SEQ ID NO 3
<211> LENGTH: 122
<212> TYPE: PRT
<213> ORGANISM: Mus musculus

<400> SEQUENCE: 3

Met Ile Gln Arg Gly Arg Ala Thr Leu Leu Val Ala Leu Leu Leu Leu
1               5                   10                  15

Ala Gln Leu Arg Pro Glu Ser Ser Gln Trp Ser Pro Ala Ala Ala Ala
            20                  25                  30

Ala Thr Gly Val Gln Asp Pro Asn Leu Arg Trp Ser Pro Gly Val Arg
        35                  40                  45

Asn Gln Gly Gly Gly Val Arg Ala Leu Leu Leu Leu Ala Glu Arg
    50                  55                  60

Phe Pro Arg Arg Ala Gly Ser Glu Pro Ala Gly Glu Arg Gln Arg Arg
65                  70                  75                  80

Asp Asp Pro Pro Leu Ser Ile Asp Leu Thr Phe His Leu Leu Arg Thr
                85                  90                  95

Leu Leu Glu Leu Ala Arg Thr Gln Ser Gln Arg Glu Arg Ala Glu Gln
            100                 105                 110

Asn Arg Ile Ile Phe Asp Ser Val Gly Lys
        115                 120

<210> SEQ ID NO 4
<211> LENGTH: 127
<212> TYPE: PRT
<213> ORGANISM: Sus scrofa

<400> SEQUENCE: 4
```

Met Arg Pro Ala Gly Leu Ala Leu Leu Ala Leu Leu Leu Leu
1               5                   10                  15

Ala Gln Leu Arg Pro Gly Ser Ser Gln Trp Ser Pro Glu Ala Ala Val
            20                  25                  30

Ala Gly Val Gln Asp Pro Ser Leu Arg Trp Ser Pro Arg Thr Gln Lys
            35                  40                  45

His Gly Ser Gly Ala Arg Ala Leu Leu Leu Leu Ala Glu Arg
    50                  55                  60

Phe Pro Arg Arg Ala Gly Gln Gly Arg Trp Gly Ser Gly Ala Ala Ser
65              70                  75                  80

Glu Arg Pro Arg Arg Asp Asp Pro Leu Ser Ile Asp Leu Thr Phe
            85                  90                  95

His Leu Leu Arg Thr Leu Leu Glu Leu Ala Arg Thr Gln Ser Gln Arg
            100                 105                 110

Glu Arg Ala Glu Gln Asn Arg Ile Ile Phe Asp Ser Val Gly Lys
            115                 120                 125

<210> SEQ ID NO 5
<211> LENGTH: 122
<212> TYPE: PRT
<213> ORGANISM: Cricetulus griseus

<400> SEQUENCE: 5

Met Arg Gln Arg Gly Arg Ala Ala Leu Leu Val Ala Leu Leu Leu Leu
1               5                   10                  15

Ala Gln Leu Arg Pro Gly Ser Ser Gln Trp Ser Pro Ala Thr Glu Ala
            20                  25                  30

Ala Thr Gly Val Gln Asp Pro Asn Leu Arg Trp Ser Pro Gly Ala Arg
            35                  40                  45

Asn Gln Gly Gly Gly Ala Arg Ala Leu Leu Leu Leu Ala Glu Arg
        50                  55                  60

Phe Pro Arg Arg Ala Gly Ser Gly Thr Ala Gly Glu Arg Gln Arg Arg
65              70                  75                  80

Asp Asp Pro Pro Leu Ser Ile Asp Leu Thr Phe His Leu Leu Arg Thr
            85                  90                  95

Leu Leu Glu Leu Ala Arg Thr Gln Ser Gln Arg Glu Arg Ala Glu Gln
            100                 105                 110

Asn Arg Ile Ile Leu Asn Ala Val Gly Lys
            115                 120

<210> SEQ ID NO 6
<211> LENGTH: 122
<212> TYPE: PRT
<213> ORGANISM: Rattus norvegicus

<400> SEQUENCE: 6

Met Arg Gln Arg Gly Arg Ala Thr Leu Leu Val Ala Leu Leu Leu Leu
1               5                   10                  15

Val Gln Leu Arg Pro Glu Ser Ser Gln Trp Ser Pro Ala Ala Ala Ala
            20                  25                  30

Ala Asn Val Val Gln Asp Pro Asn Leu Arg Trp Asn Pro Gly Val Arg
            35                  40                  45

Asn Gln Gly Gly Gly Val Arg Ala Leu Leu Leu Leu Ala Glu Arg
        50                  55                  60

Phe Pro Arg Arg Ala Gly Ser Glu Pro Ala Gly Glu Arg Gln Arg Arg
65              70                  75                  80

Asp Asp Pro Pro Leu Ser Ile Asp Leu Thr Phe His Leu Leu Arg Thr
            85                  90                  95

Leu Leu Glu Leu Ala Arg Thr Gln Ser Gln Arg Glu Arg Ala Glu Gln
        100                 105                 110

Asn Arg Ile Ile Phe Asp Ser Val Gly Lys
        115                 120

<210> SEQ ID NO 7
<211> LENGTH: 40
<212> TYPE: PRT
<213> ORGANISM: Homo sapiens

<400> SEQUENCE: 7

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 8
<211> LENGTH: 40
<212> TYPE: PRT
<213> ORGANISM: Bos taurus

<400> SEQUENCE: 8

Asp Asp Pro Pro Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 9
<211> LENGTH: 40
<212> TYPE: PRT
<213> ORGANISM: Mus musculus

<400> SEQUENCE: 9

Asp Asp Pro Pro Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 10
<211> LENGTH: 40
<212> TYPE: PRT
<213> ORGANISM: Sus scrofa

<400> SEQUENCE: 10

Asp Asp Pro Pro Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 11

```
<211> LENGTH: 40
<212> TYPE: PRT
<213> ORGANISM: Cricetulus griseus

<400> SEQUENCE: 11

Asp Asp Pro Pro Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Leu Asn Ala Val
            35                  40

<210> SEQ ID NO 12
<211> LENGTH: 40
<212> TYPE: PRT
<213> ORGANISM: Rattus norvegicus

<400> SEQUENCE: 12

Asp Asp Pro Pro Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
            35                  40

<210> SEQ ID NO 13
<211> LENGTH: 161
<212> TYPE: PRT
<213> ORGANISM: Homo sapiens

<400> SEQUENCE: 13

Met Leu Met Pro Val His Phe Leu Leu Leu Leu Leu Leu Leu Leu Gly
1               5                   10                  15

Gly Pro Arg Thr Gly Leu Pro His Lys Phe Tyr Lys Ala Lys Pro Ile
            20                  25                  30

Phe Ser Cys Leu Asn Thr Ala Leu Ser Glu Ala Glu Lys Gly Gln Trp
        35                  40                  45

Glu Asp Ala Ser Leu Leu Ser Lys Arg Ser Phe His Tyr Leu Arg Ser
    50                  55                  60

Arg Asp Ala Ser Ser Gly Glu Glu Glu Gly Lys Glu Lys Lys Thr
65                  70                  75                  80

Phe Pro Ile Ser Gly Ala Arg Gly Gly Ala Arg Gly Thr Arg Tyr Arg
                85                  90                  95

Tyr Val Ser Gln Ala Gln Pro Arg Gly Lys Pro Arg Gln Asp Thr Ala
            100                 105                 110

Lys Ser Pro His Arg Thr Lys Phe Thr Leu Ser Leu Asp Val Pro Thr
        115                 120                 125

Asn Ile Met Asn Leu Leu Phe Asn Ile Ala Lys Ala Lys Asn Leu Arg
    130                 135                 140

Ala Gln Ala Ala Ala Asn Ala His Leu Met Ala Gln Ile Gly Arg Lys
145                 150                 155                 160

Lys

<210> SEQ ID NO 14
<211> LENGTH: 129
<212> TYPE: PRT
<213> ORGANISM: Bos taurus

<400> SEQUENCE: 14
```

```
Met Lys Thr Ala Gly Arg Ala Ala Leu Leu Ala Leu Leu Leu Leu
1               5                   10                  15

Ala Gln Leu Arg Pro Gly Ser Ser Gln Trp Ser Glu Glu Ala
            20                  25                  30

Ala Ala Ala Gly Val Arg Asp Pro Arg Leu Arg Trp Ser Pro Gly Thr
            35                  40                  45

Arg Asn His Gly Gly Gly Ala Arg Ala Leu Leu Leu Leu Ala Glu
65  50              55                      60

Arg Phe Pro Arg Arg Ala Glu Gln Gly Arg Trp Gly Ser Gly Thr
65              70                  75                  80

Ala Gly Glu Arg Pro Arg Arg Asp Asp Pro Leu Ser Ile Asp Leu
                85                  90                  95

Thr Phe His Leu Leu Arg Thr Leu Leu Glu Leu Ala Arg Thr Gln Ser
                100                 105                 110

Gln Arg Glu Arg Ala Glu Gln Asn Arg Ile Ile Phe Asp Ser Val Gly
            115                 120                 125

Lys
```

<210> SEQ ID NO 15
<211> LENGTH: 164
<212> TYPE: PRT
<213> ORGANISM: Mus musculus

<400> SEQUENCE: 15

```
Met Leu Met Pro Thr Tyr Phe Leu Leu Pro Leu Leu Leu Leu Gly
1               5                   10                  15

Gly Pro Arg Thr Ser Leu Ser His Lys Phe Tyr Asn Thr Gly Pro Val
            20                  25                  30

Phe Ser Cys Leu Asn Thr Ala Leu Ser Glu Val Lys Lys Asn Lys Leu
            35                  40                  45

Glu Asp Val Pro Leu Leu Ser Lys Lys Ser Phe Gly His Leu Pro Thr
50                      55                  60

Gln Asp Pro Ser Gly Glu Glu Asp Asn Gln Thr His Leu Gln Ile
65                  70                      75                  80

Lys Arg Thr Phe Ser Gly Ala Ala Gly Gly Asn Gly Ala Gly Ser Thr
                85                  90                  95

Arg Tyr Arg Tyr Gln Ser Gln Ala Gln His Lys Gly Lys Leu Tyr Pro
                100                 105                 110

Asp Lys Pro Lys Ser Asp Arg Gly Thr Lys Phe Thr Leu Ser Leu Asp
            115                 120                 125

Val Pro Thr Asn Ile Met Asn Ile Leu Phe Asn Ile Asp Lys Ala Lys
            130                 135                 140

Asn Leu Arg Ala Lys Ala Ala Ala Asn Ala Gln Leu Met Ala Gln Ile
145                 150                 155                 160

Gly Lys Lys Lys
```

<210> SEQ ID NO 16
<211> LENGTH: 164
<212> TYPE: PRT
<213> ORGANISM: Rattus norvegicus

<400> SEQUENCE: 16

```
Met Leu Met Pro Thr Tyr Phe Leu Leu Leu Leu Leu Leu Leu Gly
1               5                   10                  15

Gly Pro Arg Thr Ser Leu Ser His Lys Phe Tyr Asn Ala Gly Pro Val
```

```
                    20                  25                  30

Phe Ser Cys Leu Asn Thr Ala Leu Ser Glu Val Lys Lys Asn Lys Leu
            35                  40                  45

Glu Asp Val Pro Val Leu Ser Lys Lys Asn Phe Gly Tyr Leu Pro Thr
 50                  55                  60

Gln Asp Pro Ser Gly Glu Glu Asp Glu Gln Lys His Ile Lys Asn
 65                  70                  75                  80

Lys Arg Thr Phe Ser Asp Ala Val Gly Asn Gly Gly Arg Ser Ile
                 85                  90                  95

Arg Tyr Arg Tyr Gln Ser Gln Ala Gln Pro Lys Gly Lys Leu Tyr Pro
                100                 105                 110

Asp Lys Val Lys Asn Asp Arg Gly Thr Lys Phe Thr Leu Ser Leu Asp
            115                 120                 125

Val Pro Thr Asn Ile Met Asn Ile Leu Phe Asn Ile Asp Lys Ala Lys
        130                 135                 140

Asn Leu Arg Ala Lys Ala Ala Asn Ala Gln Leu Met Ala Gln Ile
145                 150                 155                 160

Gly Lys Lys Lys

<210> SEQ ID NO 17
<211> LENGTH: 112
<212> TYPE: PRT
<213> ORGANISM: Homo sapiens

<400> SEQUENCE: 17

Met Thr Arg Cys Ala Leu Leu Leu Met Val Leu Met Leu Gly Arg
 1               5                  10                  15

Val Leu Val Val Pro Val Thr Pro Ile Pro Thr Phe Gln Leu Arg Pro
                 20                  25                  30

Gln Asn Ser Pro Gln Thr Thr Pro Arg Pro Ala Ala Ser Glu Ser Pro
            35                  40                  45

Ser Ala Ala Pro Thr Trp Pro Trp Ala Ala Gln Ser His Cys Ser Pro
        50                  55                  60

Thr Arg His Pro Gly Ser Arg Ile Val Leu Ser Leu Asp Val Pro Ile
 65                  70                  75                  80

Gly Leu Leu Gln Ile Leu Leu Glu Gln Ala Arg Ala Arg Ala Arg
                 85                  90                  95

Glu Gln Ala Thr Thr Asn Ala Arg Ile Leu Ala Arg Val Gly His Cys
            100                 105                 110

<210> SEQ ID NO 18
<211> LENGTH: 112
<212> TYPE: PRT
<213> ORGANISM: Bos taurus

<400> SEQUENCE: 18

Met Thr Arg Cys Ala Leu Val Leu Leu Met Val Leu Lys Leu Gly Arg
 1               5                  10                  15

Thr Leu Leu Val Pro Ala Thr Pro Ile Pro Gly Phe Gln Leu Leu Pro
                 20                  25                  30

Gln Asn Phe Pro Gln Ala Thr Ala Cys Pro Val Thr Ser Glu Ser Pro
            35                  40                  45

Ser Gly Ser Thr Thr Ala Pro Ser Ala Ala Trp Gly Arg Pro Ser Pro
        50                  55                  60

Asp Pro His Pro Gly Pro Arg Ile Thr Leu Ser Leu Asp Val Pro Leu
 65                  70                  75                  80
```

```
Gly Leu Leu Gln Ile Leu Leu Glu Gln Ala Arg Ala Arg Ala Val Arg
                85                  90                  95

Glu Gln Ala Ala Ala Asn Ala Arg Ile Leu Ala His Val Gly His Arg
            100                 105                 110
```

<210> SEQ ID NO 19
<211> LENGTH: 113
<212> TYPE: PRT
<213> ORGANISM: Mus musculus

<400> SEQUENCE: 19

```
Met Met Thr Arg Trp Ala Leu Val Val Phe Val Val Leu Met Leu Asp
1               5                   10                  15

Arg Ile Leu Phe Val Pro Gly Thr Pro Ile Pro Thr Phe Gln Leu Leu
                20                  25                  30

Pro Gln Asn Ser Leu Glu Thr Thr Pro Ser Ser Val Thr Ser Glu Ser
            35                  40                  45

Ser Ser Gly Thr Thr Thr Gly Pro Ser Ala Ser Trp Ser Asn Ser Lys
        50                  55                  60

Ala Ser Pro Tyr Leu Asp Thr Arg Val Ile Leu Ser Leu Asp Val Pro
65                  70                  75                  80

Ile Gly Leu Leu Arg Ile Leu Leu Glu Gln Ala Arg Tyr Lys Ala Ala
                85                  90                  95

Arg Asn Gln Ala Ala Thr Asn Ala Gln Ile Leu Ala His Val Gly Arg
            100                 105                 110

Arg
```

<210> SEQ ID NO 20
<211> LENGTH: 110
<212> TYPE: PRT
<213> ORGANISM: Rattus norvegicus

<400> SEQUENCE: 20

```
Met Met Thr Arg Trp Ala Leu Val Val Phe Met Val Leu Met Leu Asp
1               5                   10                  15

Arg Val Pro Gly Thr Pro Ile Pro Thr Phe Gln Leu Leu Pro Gln Asn
                20                  25                  30

Tyr Pro Glu Thr Thr Pro Ser Ser Val Ser Ser Glu Ser Pro Ser Asp
            35                  40                  45

Thr Thr Thr Gly Pro Ser Ala Ser Trp Ser Asn Ser Lys Ala Ser Pro
        50                  55                  60

Tyr Leu Asp Thr Arg Val Ile Leu Ser Leu Asp Val Pro Ile Gly Leu
65                  70                  75                  80

Leu Arg Ile Leu Leu Glu Gln Ala Arg Asn Lys Ala Ala Arg Asn Gln
                85                  90                  95

Ala Ala Thr Asn Ala Gln Ile Leu Ala Arg Val Gly Arg Arg
            100                 105                 110
```

<210> SEQ ID NO 21
<211> LENGTH: 38
<212> TYPE: PRT
<213> ORGANISM: Homo sapiens

<400> SEQUENCE: 21

```
Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
```

His Leu Met Ala Gln Ile
        35

<210> SEQ ID NO 22
<211> LENGTH: 38
<212> TYPE: PRT
<213> ORGANISM: Bos taurus

<400> SEQUENCE: 22

Val Thr Leu Ser Leu Asp Val Pro Thr Asn Ile Met Asn Ile Leu Phe
1               5                   10                  15

Asn Ile Ala Lys Ala Lys Asn Leu Arg Ala Lys Ala Ala Ala Asn Ala
            20                  25                  30

His Leu Met Ala Gln Ile
        35

<210> SEQ ID NO 23
<211> LENGTH: 38
<212> TYPE: PRT
<213> ORGANISM: Mus musculus

<400> SEQUENCE: 23

Phe Thr Leu Ser Leu Asp Val Pro Thr Asn Ile Met Asn Ile Leu Phe
1               5                   10                  15

Asn Ile Asp Lys Ala Lys Asn Leu Arg Ala Lys Ala Ala Ala Asn Ala
            20                  25                  30

Gln Leu Met Ala Gln Ile
        35

<210> SEQ ID NO 24
<211> LENGTH: 38
<212> TYPE: PRT
<213> ORGANISM: Rattus norvegicus

<400> SEQUENCE: 24

Phe Thr Leu Ser Leu Asp Val Pro Thr Asn Ile Met Asn Ile Leu Phe
1               5                   10                  15

Asn Ile Asp Lys Ala Lys Asn Leu Arg Ala Lys Ala Ala Ala Asn Ala
            20                  25                  30

Gln Leu Met Ala Gln Ile
        35

<210> SEQ ID NO 25
<211> LENGTH: 38
<212> TYPE: PRT
<213> ORGANISM: Homo sapiens

<400> SEQUENCE: 25

Ile Val Leu Ser Leu Asp Val Pro Ile Gly Leu Leu Gln Ile Leu Leu
1               5                   10                  15

Glu Gln Ala Arg Ala Arg Ala Arg Glu Gln Ala Thr Thr Asn Ala
            20                  25                  30

Arg Ile Leu Ala Arg Val
        35

<210> SEQ ID NO 26
<211> LENGTH: 38
<212> TYPE: PRT
<213> ORGANISM: Bos taurus

```
<400> SEQUENCE: 26

Ile Thr Leu Ser Leu Asp Val Pro Leu Gly Leu Leu Gln Ile Leu Leu
1               5                   10                  15

Glu Gln Ala Arg Ala Arg Ala Val Arg Glu Gln Ala Ala Ala Asn Ala
            20                  25                  30

Arg Ile Leu Ala His Val
            35

<210> SEQ ID NO 27
<211> LENGTH: 38
<212> TYPE: PRT
<213> ORGANISM: Mus musculus

<400> SEQUENCE: 27

Val Ile Leu Ser Leu Asp Val Pro Ile Gly Leu Leu Arg Ile Leu Leu
1               5                   10                  15

Glu Gln Ala Arg Tyr Lys Ala Ala Arg Asn Gln Ala Ala Thr Asn Ala
            20                  25                  30

Gln Ile Leu Ala His Val
            35

<210> SEQ ID NO 28
<211> LENGTH: 38
<212> TYPE: PRT
<213> ORGANISM: Rattus norvegicus

<400> SEQUENCE: 28

Val Ile Leu Ser Leu Asp Val Pro Ile Gly Leu Leu Arg Ile Leu Leu
1               5                   10                  15

Glu Gln Ala Arg Asn Lys Ala Ala Arg Asn Gln Ala Ala Thr Asn Ala
            20                  25                  30

Gln Ile Leu Ala Arg Val
            35

<210> SEQ ID NO 29
<211> LENGTH: 196
<212> TYPE: PRT
<213> ORGANISM: Homo sapiens

<400> SEQUENCE: 29

Met Arg Leu Pro Leu Leu Val Ser Ala Gly Val Leu Leu Val Ala Leu
1               5                   10                  15

Leu Pro Cys Pro Pro Cys Arg Ala Leu Leu Ser Arg Gly Pro Val Pro
            20                  25                  30

Gly Ala Arg Gln Ala Pro Gln His Pro Gln Pro Leu Asp Phe Phe Gln
            35                  40                  45

Pro Pro Pro Gln Ser Glu Gln Pro Gln Gln Pro Gln Ala Arg Pro Val
        50                  55                  60

Leu Leu Arg Met Gly Glu Glu Tyr Phe Leu Arg Leu Gly Asn Leu Asn
65                  70                  75                  80

Lys Ser Pro Ala Ala Pro Leu Ser Pro Ala Ser Ser Leu Leu Ala Gly
                85                  90                  95

Gly Ser Gly Ser Arg Pro Ser Pro Glu Gln Ala Thr Ala Asn Phe Phe
            100                 105                 110

Arg Val Leu Leu Gln Gln Leu Leu Pro Arg Arg Ser Leu Asp Ser
            115                 120                 125

Pro Ala Ala Leu Ala Glu Arg Gly Ala Arg Asn Ala Leu Gly Gly His
        130                 135                 140
```

```
Gln Glu Ala Pro Glu Arg Glu Arg Ser Glu Pro Pro Ile Ser
145                 150                 155                 160

Leu Asp Leu Thr Phe His Leu Leu Arg Glu Val Leu Glu Met Ala Arg
                165                 170                 175

Ala Glu Gln Leu Ala Gln Gln Ala His Ser Asn Arg Lys Leu Met Glu
            180                 185                 190

Ile Ile Gly Lys
        195

<210> SEQ ID NO 30
<211> LENGTH: 190
<212> TYPE: PRT
<213> ORGANISM: Bos taurus
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid

<400> SEQUENCE: 30

Met Arg Leu Pro Leu Leu Val Ser Val Gly Val Leu Leu Val Ala Leu
1               5                   10                  15

Leu Pro Ser Pro Pro Cys Arg Ala Leu Leu Ser Arg Gly Pro Ile Pro
            20                  25                  30

Gly Ala Arg Gln Ala Ser Gln His Pro Gln Pro Leu Xaa Phe Phe Gln
        35                  40                  45

Pro Pro Pro Gln Pro Gln Glu Pro Gln Ala Leu Pro Thr Leu Leu Arg
    50                  55                  60

Val Gly Glu Glu Tyr Phe Leu Arg Leu Gly Asn Leu Asp Glu Thr Arg
65                  70                  75                  80

Ala Ala Pro Leu Ser Pro Ala Ala Ser Pro Leu Ala Ser Arg Ser Ser
                85                  90                  95

Ser Arg Leu Ser Pro Asp Lys Val Ala Ala Asn Phe Phe Arg Ala Leu
            100                 105                 110

Leu Gln Pro Arg Arg Pro Phe Asp Ser Pro Ala Gly Pro Ala Glu Arg
        115                 120                 125

Gly Thr Glu Asn Ala Leu Gly Ser Arg Gln Glu Ala Pro Ala Ala Arg
    130                 135                 140

Lys Arg Ser Gln Glu Pro Pro Ile Ser Leu Asp Leu Thr Phe His
145                 150                 155                 160

Leu Leu Arg Glu Val Leu Glu Met Thr Lys Ala Asp Gln Leu Ala Gln
                165                 170                 175

Gln Ala His Xaa Asn Arg Lys Leu Leu Asp Ile Ala Gly Lys
            180                 185                 190

<210> SEQ ID NO 31
<211> LENGTH: 187
<212> TYPE: PRT
<213> ORGANISM: Mus musculus

<400> SEQUENCE: 31

Met Arg Leu Arg Leu Leu Val Ser Ala Gly Met Leu Leu Val Ala Leu
1               5                   10                  15

Ser Ser Cys Leu Pro Cys Arg Ala Leu Leu Ser Arg Gly Ser Val Pro
            20                  25                  30
```

```
Arg Ala Pro Arg Ala Pro Gln Pro Leu Asn Phe Leu Gln Pro Glu Gln
            35                  40                  45

Pro Gln Gln Pro Gln Pro Val Leu Ile Arg Met Gly Glu Glu Tyr Phe
    50                  55                  60

Leu Arg Leu Gly Asn Leu Asn Arg Ser Pro Ala Ala Arg Leu Ser Pro
65                  70                  75                  80

Asn Ser Thr Pro Leu Thr Ala Gly Arg Gly Ser Arg Pro Ser His Asp
                85                  90                  95

Gln Ala Ala Ala Asn Phe Phe Arg Val Leu Leu Gln Gln Leu Gln Met
                100                 105                 110

Pro Gln Arg Ser Leu Asp Ser Arg Ala Glu Pro Ala Glu Arg Gly Ala
            115                 120                 125

Glu Asp Ala Leu Gly Gly His Gln Gly Ala Leu Glu Arg Glu Arg Arg
130                 135                 140

Ser Glu Glu Pro Pro Ile Ser Leu Asp Leu Thr Phe His Leu Leu Arg
145                 150                 155                 160

Glu Val Leu Glu Met Ala Arg Ala Glu Gln Leu Ala Gln Gln Ala His
                165                 170                 175

Ser Asn Arg Lys Leu Met Glu Ile Ile Gly Lys
            180                 185

<210> SEQ ID NO 32
<211> LENGTH: 191
<212> TYPE: PRT
<213> ORGANISM: Sus scrofa

<400> SEQUENCE: 32

Met Arg Leu Pro Leu Leu Val Ser Ala Gly Val Leu Leu Val Ala Leu
1               5                   10                  15

Leu Pro Cys Pro Pro Cys Arg Ala Leu Leu Ser Arg Gly Pro Val Leu
                20                  25                  30

Gly Ala Arg Gln Ala Pro Gln His Pro Gln Ala Leu Asp Phe Leu Gln
            35                  40                  45

Pro Gln Gln Gln Pro Gln Gln Pro Gln Pro Arg Pro Val Leu Leu Arg
    50                  55                  60

Met Gly Glu Glu Tyr Phe Leu Arg Leu Gly Asn Leu Asn Lys Ser Pro
65                  70                  75                  80

Ala Ala Pro Leu Ser Pro Ala Ser Ser Pro Leu Thr Gly Ser Ser Gly
                85                  90                  95

Asn Arg Pro Asp Glu Val Ala Ala Asn Phe Phe Arg Ala Leu Leu Gln
                100                 105                 110

Gln Leu Pro Leu Pro Arg Arg Pro Leu Asp Ser Pro Ser Gly Pro Ala
            115                 120                 125

Glu Arg Gly Ala Glu Asn Ala Leu Ser Ser Arg Gln Glu Ala Pro Glu
130                 135                 140

Arg Glu Arg Arg Ser Glu Glu Pro Pro Ile Ser Leu Asp Leu Thr Phe
145                 150                 155                 160

His Leu Leu Arg Glu Val Leu Glu Met Ala Arg Ala Glu Gln Leu Ala
                165                 170                 175

Gln Gln Ala His Ser Asn Arg Lys Leu Met Glu Ile Ile Gly Lys
            180                 185                 190

<210> SEQ ID NO 33
<211> LENGTH: 187
<212> TYPE: PRT
<213> ORGANISM: Rattus norvegicus
```

<400> SEQUENCE: 33

```
Met Arg Leu Arg Leu Leu Val Ser Ala Gly Met Leu Leu Val Ala Leu
1               5                   10                  15

Ser Pro Cys Leu Pro Cys Arg Ala Leu Leu Ser Arg Gly Ser Val Ser
            20                  25                  30

Gly Ala Pro Arg Ala Pro Gln Pro Leu Asn Phe Leu Gln Pro Glu Gln
        35                  40                  45

Pro Gln Pro Gln Pro Ile Leu Ile Arg Met Gly Glu Glu Tyr Phe
    50                  55                  60

Leu Arg Leu Gly Asn Leu Asn Arg Ser Pro Ala Ala Arg Leu Ser Pro
65                  70                  75                  80

Asn Ser Thr Pro Leu Thr Ala Gly Arg Gly Ser Arg Pro Ser His Asp
                85                  90                  95

Gln Ala Ala Ala Asn Phe Phe Arg Val Leu Leu Gln Gln Leu Gln Met
            100                 105                 110

Pro Gln Arg Pro Leu Asp Ser Ser Thr Glu Leu Ala Glu Arg Gly Ala
        115                 120                 125

Glu Asp Ala Leu Gly Gly His Gln Gly Ala Leu Glu Arg Glu Arg Arg
    130                 135                 140

Ser Glu Glu Pro Pro Ile Ser Leu Asp Leu Thr Phe His Leu Leu Arg
145                 150                 155                 160

Glu Val Leu Glu Met Ala Arg Ala Glu Gln Leu Ala Gln Gln Ala His
                165                 170                 175

Ser Asn Arg Lys Leu Met Glu Ile Ile Gly Lys
            180                 185
```

<210> SEQ ID NO 34
<211> LENGTH: 190
<212> TYPE: PRT
<213> ORGANISM: Ovis aries

<400> SEQUENCE: 34

```
Met Arg Leu Pro Leu Leu Val Ser Val Gly Val Leu Leu Val Ala Leu
1               5                   10                  15

Leu Pro Ser Pro Pro Cys Arg Ala Leu Leu Ser Arg Gly Pro Ile Pro
            20                  25                  30

Gly Ala Arg Gln Ala Ser Gln His Pro Gln Pro Leu Ser Phe Phe Gln
        35                  40                  45

Pro Leu Pro Gln Pro Gln Glu Pro Gln Ala Leu Pro Thr Leu Leu Arg
    50                  55                  60

Val Gly Glu Glu Tyr Phe Leu Arg Leu Gly Asn Leu Asp Glu Thr Arg
65                  70                  75                  80

Ala Ala Pro Leu Ser Pro Ala Ala Ser Pro Leu Ala Ser Arg Ser Ser
                85                  90                  95

Ser Arg Leu Ser Pro Asp Lys Val Ala Ala Asn Phe Phe Arg Ala Leu
            100                 105                 110

Leu Gln Pro Arg Arg Pro Leu Asp Ser Pro Ala Gly Pro Ala Lys Arg
        115                 120                 125

Gly Thr Glu Asn Ala Leu Gly Ser Arg Gln Glu Ala Pro Ala Ala Arg
    130                 135                 140

Lys Arg Arg Ser Gln Glu Pro Pro Ile Ser Leu Asp Leu Thr Phe His
145                 150                 155                 160

Leu Leu Arg Glu Val Leu Glu Met Thr Lys Ala Asp Gln Leu Ala Gln
                165                 170                 175
```

-continued

Gln Ala His Ser Asn Arg Lys Leu Leu Asp Ile Ala Gly Lys
              180                 185                 190

<210> SEQ ID NO 35
<211> LENGTH: 41
<212> TYPE: PRT
<213> ORGANISM: Homo sapiens

<400> SEQUENCE: 35

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 36
<211> LENGTH: 41
<212> TYPE: PRT
<213> ORGANISM: Bos taurus
<220> FEATURE:
<221> NAME/KEY: misc_feature
<222> LOCATION: (33)..(33)
<223> OTHER INFORMATION: Xaa can be any naturally occurring amino acid

<400> SEQUENCE: 36

Ser Gln Glu Pro Pro Ile Ser Leu Asp Leu Thr Phe His Leu Leu Arg
1               5                   10                  15

Glu Val Leu Glu Met Thr Lys Ala Asp Gln Leu Ala Gln Gln Ala His
            20                  25                  30

Xaa Asn Arg Lys Leu Leu Asp Ile Ala
        35                  40

<210> SEQ ID NO 37
<211> LENGTH: 41
<212> TYPE: PRT
<213> ORGANISM: Mus musculus

<400> SEQUENCE: 37

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 38
<211> LENGTH: 41
<212> TYPE: PRT
<213> ORGANISM: Sus scrofa

<400> SEQUENCE: 38

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 39
<211> LENGTH: 41

```
<212> TYPE: PRT
<213> ORGANISM: Rattus norvegicus

<400> SEQUENCE: 39

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 40
<211> LENGTH: 41
<212> TYPE: PRT
<213> ORGANISM: Ovis aries

<400> SEQUENCE: 40

Ser Gln Glu Pro Pro Ile Ser Leu Asp Leu Thr Phe His Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 41
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (18)..(18)
<223> OTHER INFORMATION: X = Nle
<220> FEATURE:
<221> NAME/KEY: MISC_FEATURE
<222> LOCATION: (35)..(35)
<223> OTHER INFORMATION: X = Nle

<400> SEQUENCE: 41

Pro Pro Ile Ser Leu Asp Leu Thr Phe His Leu Leu Arg Glu Val Leu
1               5                   10                  15

Glu Xaa Ala Arg Ala Glu Gln Leu Ala Gln Gln Glu His Ser Lys Arg
            20                  25                  30

Lys Leu Xaa Glu Ile Ile
        35
```

METHODS FOR INCREASING INSULIN SECRETION BY CO-STIMULATION OF CORTICOTROPIN-RELEASING FACTOR RECEPTORS

This application claims the benefit of U.S. Provisional Patent Application No. 61/550,754, filed Oct. 24, 2011, the entirety of which is incorporated herein by reference.

The invention was made with government support under Grant No. 5P01DK026741-32 awarded by the National Institutes of Health. The government has certain rights in the invention.

BACKGROUND OF THE INVENTION

1. Field of the Invention

The present invention relates generally to the field of molecular biology and endocrinology. More particularly, it concerns methods for the treatment of elevated serum glucose and diabetes mellitus.

2. Description of Related Art

Regulation of glucose homeostasis in the bloodstream must be tightly controlled to maintain healthy metabolic function. Low serum glucose levels (hypoglycemia) can lead to weakness, headaches, confusion, and if unchecked, ultimately convulsions, coma, and death. On the other hand, hyperglycemia causes excess urine production, thirst, weight loss, fatigue, and in severe cases can also result in coma and death. Chronically high blood sugar also causes long term tissue damage that may contribute to diabetic complications, such as blindness, kidney failure, impotence, atherosclerosis, and increased vulnerability to infection.

In a healthy subject, pancreatic tissue is responsible for secretion of hormones that regulate serum glucose homeostasis. After a meal, when blood glucose levels rise, secretion of insulin lowers blood sugar by stimulating tissue glucose uptake (the primary tissue responsible being skeletal muscle). Conversely, when serum glucose levels fall, secretion of glucagon stimulates the liver to release stored glucose into the blood stream.

Diabetes mellitus is an increasingly common disorder around the world, characterized by chronically elevated serum glucose levels. Classically, diabetes segregates into two distinct groups that require alternative therapeutic approaches. Type 1 diabetes, is primarily caused by an inability of the subject to produce sufficient insulin to regulate blood sugar. On the other hand, type 2 diabetes is characterized by a reduced ability to respond to serum insulin, a state know as insulin resistance. Treatment of both types of diabetes can involve the administration of insulin, however, frequent insulin injections are both expensive and burdensome, involving the need for constant blood sugar assessment to regulate and time insulin dosing.

SUMMARY OF THE INVENTION

In a first embodiment a method for stimulating insulin secretion or increasing beta cell mass in a subject is provided comprising administering to the subject an effective amount of a $CRF_1$ receptor agonist and a $CRF_2$ receptor agonist. In a further embodiment a method is provided for preventing loss of beta cells in a subject comprising administering to the subject an effective amount of a $CRF_1$ receptor agonist and a $CRF_2$ receptor agonist. In certain aspects, the subject is a subject with diabetes mellitus (e.g., type I or type II diabetes mellitus). Thus, in some aspects, a method of the embodiments can be defined as a method for treating diabetes in a subject comprising administering to the subject an effective amount of a $CRF_1$ receptor agonist and a $CRF_2$ receptor agonist. As used herein "increasing beta cell mass" refers to an increased number of beta cells in a treated subject relative to the number before therapy was applied. An increase in beta cell mass can result, for example, from increased beta cell proliferation, a decrease in beta cell death (e.g., via apoptosis), or a differentiation of non-beta cells into beta cells.

In some aspects, an "effective amount" refers to an amount of a $CRF_1$ receptor agonist and a $CRF_2$ receptor agonist, that together are effective when administered to a subject to increase insulin secretion or total serum insulin levels in response to an increase in serum glucose. In some aspects, an "effective amount" refers to an amount of a $CRF_1$ receptor agonist and a $CRF_2$ receptor agonist, that together are effective when administered to a subject (e.g., when administered over a period of time) to increase beta cell mass in the subject. For example, an increased beta cell mass can be assessed by directly measuring an increase in beta cells in the subject or by determining an increase in beta cells by detecting an increased level of a product of the beta cells, such as insulin. In some aspects, an increase in beta cell mass in a subject is determined after at least 1 week, 2 weeks, 3 weeks, 1 month, 2 months, 3 months, 4 months 5 months, 6 months, or more or periodic administration of a therapy of the embodiments.

A variety of $CRF_1$ receptor agonists and $CRF_2$ receptor agonists are known in the art and can be used in accordance with the embodiments. In some aspects, the $CRF_1$ receptor agonist and the $CRF_2$ receptor agonist are the same molecule (i.e., a molecule with agonist activity relative to both receptors). For example, the $CRF_1$ receptor agonist and the $CRF_2$ receptor agonist can be a Urotensin 1 (U1) polypeptide, a sauvagine (Svg) polypeptide, or a Urocortin 1 (Ucn 1) polypeptide, such as human Ucn 1. In further aspects, the $CRF_1$ receptor agonist and/or $CRF_2$ receptor agonist is an agonist that is selective for the $CRF_1$ receptor or the $CRF_2$ receptor. Thus, in certain aspects, a method of the embodiments can comprise administering an effective amount of a selective $CRF_1$ receptor agonist and a selective $CRF_2$ receptor agonist to a subject. Examples of selective $CRF_1$ receptor agonists include, without limitation, stressin$_1$-A, cortagine, or a corticotropin-releasing factor (CRF) polypeptide, such as human CRF. Selective $CRF_2$ receptor agonists include, but are not limited to, a Urocortin 2 (Ucn 2) polypeptide or a Urocortin 3 (Ucn 3) polypeptide, such as human Ucn 2 or Ucn 3.

In some aspects of the embodiments a $CRF_1$ receptor agonist is administered to a subject before, after, or essentially simultaneously with a $CRF_2$ receptor agonist. For example, a $CRF_1$ receptor agonist can be administered to a subject about or less than about 1 day, 12 hours, 8 hours, 6 hours, 4 hours, 2 hours, 1 hour, 30 minutes, 15 minutes, 10 minutes, 5 minutes, or 1 minute before or after a $CRF_2$ receptor agonist is administered to the subject. Thus, in certain aspects, the $CRF_1$ receptor agonist and the $CRF_2$ receptor agonist are formulated together in a pharmaceutical composition. In some aspects, a therapy of the embodiments (e.g., administration of a $CRF_1$ receptor agonist and a $CRF_2$ receptor agonist) is repeated periodically, such as hourly, twice a day, daily, every two days, every three days, or weekly.

In certain aspects, a subject for treatment in accordance with the embodiments is a human subject. For example, the subject can be a subject who has diabetes, has been diagnosed with diabetes, or is at risk for developing diabetes (e.g., a subject with elevated blood sugar levels). In certain aspects, the subject has or is at risk of developing type I diabetes, but still has the ability to produce insulin or still has pancreatic beta cells. In some aspects, the subject for treatment has received or is receiving a transplant of islet cells or a stem cell therapy to restore islet cells. In further aspects, the subject has type II diabetes, is diagnosed with type II diabetes or is at risk for developing type II diabetes.

In a further embodiment a pharmaceutical composition is provided comprising a selective $CRF_1$ receptor agonist and a selective $CRF_2$ receptor agonist. The $CRF_1$ receptor agonist and selective $CRF_2$ receptor agonist can be selected from any of those known in the art or detailed herein. In certain aspects, a pharmaceutical composition of the embodiments comprises a $CRF_1$ receptor agonist and $CRF_2$ receptor agonist in a molar ratio of from about 10:1 to about 1:10; about 5:1 to about 1:5; about 2:1 to about 1:2 or about 1:1.

Methods according to the instant invention may also be used in combination with other therapeutic strategies known to those of skill in the art. For example, in certain embodiments, methods according the instant invention may be used in combination with insulin administration. Other compounds that are known in the art to be effective for regulating glucose homeostasis include sulfonylureas, alpha-glucosidase inhibitors, thiazolidinediones, metformin, and repaglinide. Thus, methods of the embodiments can comprise administering an anti-diabetes therapy to a subject in conjunction with a $CRF_1$ receptor agonist and a $CRF_2$ receptor agonist. In this case, such methods may reduce the dosage amount or administration frequency of an anti-diabetes therapy. Accordingly, in certain aspects, a method of the embodiments is defined as a method of reducing the dosage or administration frequency of an anti-diabetes therapy in a subject comprising administering to the subject a $CRF_1$ receptor agonist and a $CRF_2$ receptor agonist, which together are effective to reduce the dosage or administration frequency of an anti-diabetes therapy. Such combination treatment may be particularly preferred as reducing the effective concentrations of an anti-diabetes therapy can limit undesirable side effects of such therapy.

In a further embodiment there is provided a method of culturing cells comprising obtaining cells and culturing said cells in a media (e.g., a defined media) comprising an exogenous $CRF_1$ receptor agonist and/or an exogenous $CRF_2$ receptor agonist. For example, beta cells, such as beta cells comprised in islet tissue or beta cells produced ex vivo from pluripotent cells can be cultured according to the embodiments. In further aspects, pluripotent cells, such as embryonic stem cells or induced pluripotent stem cells (iPS cells), are cultured in accordance with the embodiments. Thus, in some aspects, a cell culture method of the embodiments is defined as a method of promoting beta cell formation.

As used herein the terms "encode" or "encoding" with reference to a nucleic acid are used to make the invention readily understandable by the skilled artisan; however, these terms may be used interchangeably with "comprise" or "comprising," respectively.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2: An amino acid alignment between Urocortin 1 coding sequences from various organisms. Amino acid sequences shown are from *Homo sapiens* (NCBI accession no. AAC24204; SEQ ID NO: 1), *Bos taurus* (NCBI accession no. NP_001027472; SEQ ID NO: 2), *Mus musculus* (NCBI accession no. AAC24202; SEQ ID NO: 3), *Sus scrofa* (NCBI accession no. AEB40202; SEQ ID NO: 4), *Cricetulus griseus* (NCBI accession no. EGV95874; SEQ ID NO: 5), and *Rattus norvegicus* (NCBI accession no. EDM02930; SEQ ID NO: 6). The predicted mature peptide sequence is shown in bold (SEQ ID NOs: 7-12, respectively).

FIG. 3: An amino acid alignment between Urocortin 2 and Urocortin 3 coding sequences from various organisms. Amino acid sequences shown are from *Homo sapiens* Ucn 3 (NCBI accession no. NP_444277; SEQ ID NO: 13), *Bos taurus* Ucn 3 (NCBI accession no. NP_001027472; SEQ ID NO: 14), *Mus musculus* Ucn 3 (NCBI accession no. NP_112540; SEQ ID NO: 15), *Rattus norvegicus* Ucn 3 (NCBI accession no. ABM45865; SEQ ID NO: 16), *Homo sapiens* Ucn 2 (NCBI accession no. NP_149976; SEQ ID NO: 17), *Bos taurus* Ucn 2 (NCBI accession no. BAF30968; SEQ ID NO: 18), *Mus musculus* Ucn 2 (NCBI accession no. NP_659543; SEQ ID NO: 19), and *Rattus norvegicus* Ucn 2 (NCBI accession no. ABM45864; SEQ ID NO: 20). The predicted mature peptide sequence is shown in bold (SEQ ID NOs: 21-28, respectively).

FIG. 4: An amino acid alignment between corticotropin-releasing factor (CRF) coding sequences from various organisms. Amino acid sequences shown are from *Homo sapiens* (NCBI accession no. CAA23834; SEQ ID NO: 29), *Bos taurus* (NCBI accession no. NP_001013418; SEQ ID NO: 30), *Mus musculus* (NCBI accession no. AAI19037; SEQ ID NO: 31), *Sus scrofa* (NCBI accession no. NP_001106533; SEQ ID NO: 32), *Rattus norvegicus* (NCBI accession no. NP_112281; SEQ ID NO: 33), and *Ovis aries* (NCBI accession no. AAA31512; SEQ ID NO: 34). The predicted mature peptide sequence is shown in bold (SEQ ID NOs: 35-40, respectively).

DESCRIPTION OF ILLUSTRATIVE EMBODIMENTS

I. The Present Invention

Diabetes mellitus, a disease that cause elevated levels of serum glucose, is currently one of the most prevalent chronic diseases, especially in Western countries. Therapies for type 1 and type 2 diabetes vary greatly, but in both cases exogenous insulin administration is often the primary therapeutic approach. However, constant administration of insulin is costly and cumbersome. Insulin administration typically requires frequent assessment of blood sugar to determine the dosage and administration schedule, and the insulin itself is typically administered by injection or infusion. In view of these therapeutic impediments, methods for enhancing a patient's ability to produce their own insulin would be desirable.

Figure 1:
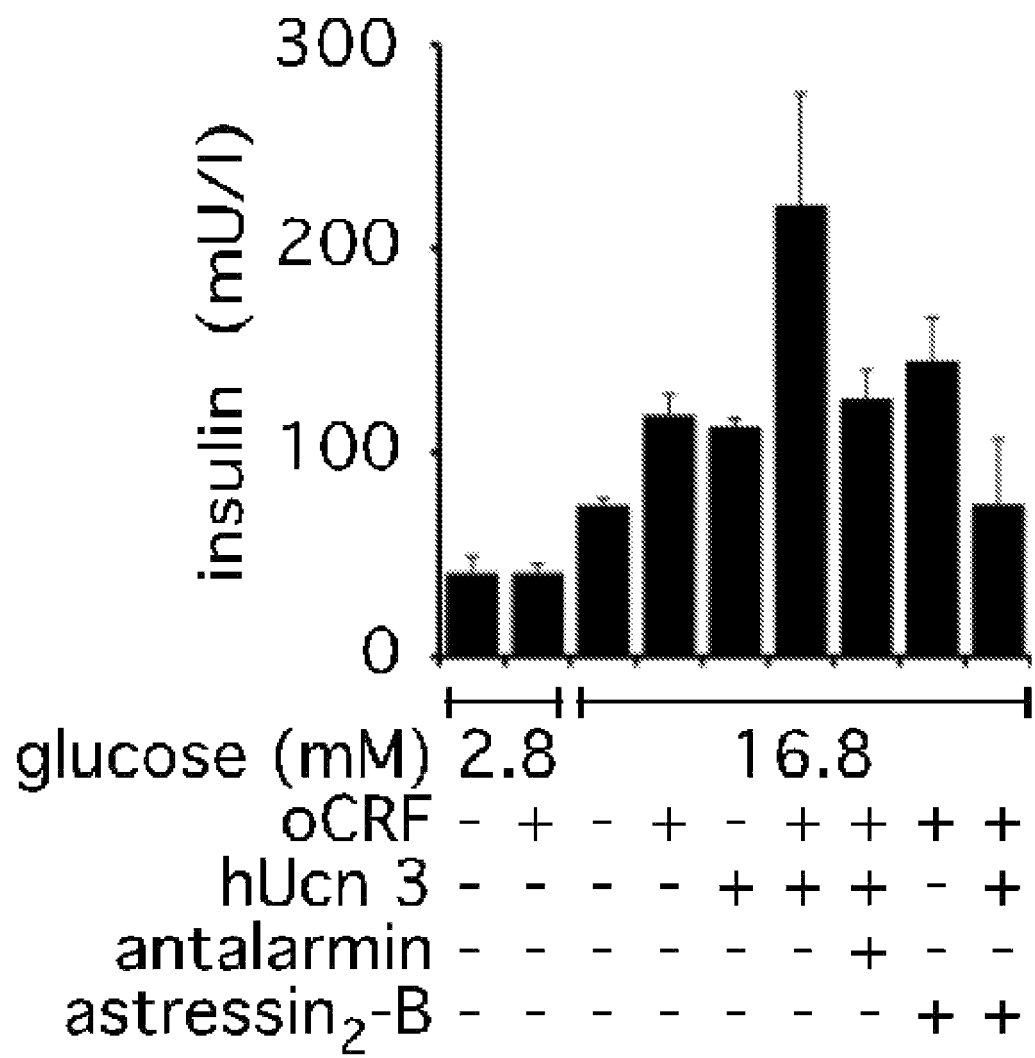
FIG. 1: Synergism of $CRF_1$ receptor and $CRF_2$ receptor signaling in human islets. Graph shows the results of studies on cultured human islet cells. Insulin secretion from the cells was assessed in the presence of low glucose (2.8 mM) or high glucose (16.8 mM) and in the presence of various CRF receptor ligands as indicated.

As detailed below, the inventors have demonstrated that, when activated in combination, $CRF_1$ receptors and $CRF_2$ receptors are able to synergistically enhance insulin secretion from human islet cultures. In particular, as shown in FIG. 1, when cultured human islets were contacted with a $CRF_1$ receptor agonist (oCRF) and a $CRF_2$ receptor agonist (hUcn 3) in the presence of glucose a significant increase in insulin secretion was observed. The level of insulin secretion upon co-stimulation was far greater than that observed with either agonist alone. Moreover, the synergistic enhancement of insulin secretion was reversed in the presence of an antagonist of either the $CRF_1$ receptor or the $CRF_2$ receptor. In addition, long-term co-stimulation of the $CRF_1$ receptor and the $CRF_2$ receptor in vivo by controlled expression of Ucn1 in mice resulted in an increase in total beta cell mass. Thus, co-stimulation of these receptors in a subject can both enhance glucose-dependent insulin secretion and increase the number of insulin producing cells thereby further enhancing insulin production capabilities of the treated subject. These studies indicate that $CRF_1/CRF_2$ co-stimulation offers the potential of a highly effective therapy for patients having excess blood sugar or diabetes.

Without being bound by theory it is proposed that the synergism of $CRF_1$ and $CRF_2$ receptor agonists with respect to beta cell stimulation is due to their respective activation of different pathways affecting islet cells. $CRF_1$ receptor agonist, for example, may directly or indirectly protect beta cells from death. On the other hand, $CRF_2$ receptor agonist may promote beta cell maturation. Thus, when agonists of both receptors are applied to islet cells, insulin secretion can be synergistically stimulated and over time, beta cell mass can be increased. Accordingly, co-stimulation of these receptors in vivo, such as by Ucn1 administration, can be used to increase glucose-dependent insulin secretion in the subject and to promote an increase in beta cells thereby increasing the ability of the subject to respond to and regulate blood sugar levels.

II. $CRF_1$ Receptor and $CRF_2$ Receptor Agonists

Combined $CRF_1/CRF_2$ Agonists

Certain embodiments of the invention concern molecules that comprise agonist activity on both $CRF_1$ receptors and $CRF_2$ receptors. An example of such a molecules is Urocortin 1 (see, e.g., U.S. Pat. No. 6,214,797, incorporated herein by reference). For example, the Urocortin can be a human or non-human Urocortin or a chimera of such polypeptides, see, e.g., FIG. 2, which provides an alignment of human and non-human Urocortin molecules. The sequences of fully processed forms of these Urocortins are provided as SEQ ID NOs: 7-12.

In some aspects, for example, a Urocortin molecule can comprise an amino acid sequence at least about 70%, 75%, 80%, 85%, 90%, 95%, 98%, 99%, or more identical to one of the mature Urocortin molecules of SEQ ID NOs: 7-12. In certain aspects, the Urocortin molecule comprises 1, 2, 3, 4, 5, 6, 7, 8, 9, or 10 amino acid deletions, insertions, or substitutions relative the molecules of SEQ ID NOs: 7-12. For example, the Urocortin molecule can comprise the sequence of human Urocortin (SEQ ID NO: 7) wherein 1, 2, 3, 4, 5, 6, 7, 8, 9, or 10 amino acids have been substituted for an amino acid at a corresponding position in a non-human Urocortin or for an amino acid with a similar hydrophobic index. In still further aspects, a Urocortin molecule can be modified to enhance agonism of (or binding to) a $CRF_1$ receptor and/or a $CRF_2$ receptor or to enhance the solubility or stability of the molecule (e.g., in vivo stability). For instance, 1, 2, 3, 4, 5, 6, 7, 8, 9, or 10 amino acids of a human or non-human Urocortin can be substituted for a non-natural or rare amino acid, such as one of those shown in Table 1 below. In still further aspects, the Urocortin can be cyclized, for example by the addition of a lactam bridge in the polypeptide (e.g., in the C-terminal half of the polypeptide). In yet further aspects, a Urocortin molecule can be conjugated, such as by PEGylation, to enhance its stability or solubility.

Selective $CRF_1$ Receptor Agonists

Certain aspects of the embodiments concern selective $CRF_1$ receptor agonists. One example, of such a molecule is corticotropin releasing factor (CRF). For example, the CRF can be a human or non-human CRF or a chimera of such polypeptides, see, e.g., FIG. 4, which provides an alignment of human and non-human CRF molecules. The sequences of fully processed forms of these CRF polypeptides are provided as SEQ ID NOs: 35-40.

In some aspects, for example, a CRF molecule can comprise an amino acid sequence at least about 70%, 75%, 80%, 85%, 90%, 95%, 98%, 99%, or more identical to one of the mature CRF molecules of SEQ ID NOs: 35-40. In certain aspects, the CRF molecule comprises, 1, 2, 3, 4, 5, 6, 7, 8, 9, or 10 amino acid deletions, insertions, or substitutions relative the polypeptides of SEQ ID NOs: 35-40. For example, the CRF molecule can comprise the sequence of human CRF (SEQ ID NO: 35) wherein 1, 2, 3, 4, 5, 6, 7, 8, 9, or 10 amino acids have been substituted for an amino acid at a corresponding position in a non-human CRF or for an amino acid with a similar hydrophobic index. In still further aspects, a CRF molecule can be modified to enhance agonism of (or binding to) a $CRF_1$ receptor or to enhance the solubility or stability of the molecule (e.g., in vivo stability). For instance, 1, 2, 3, 4, 5, 6, 7, 8, 9, or 10 amino acids of a human or non-human CRF can be substituted for a non-natural or rare amino acid, such as one of those shown in Table 1 below. In still further aspects, the CRF can be cyclized, for example by the addition of a lactam bridge in the polypeptide (e.g., in the C-terminal half of the polypeptide). In yet further aspects, a CRF molecule can be conjugated, such as by PEGylation, to enhance its stability or solubility.

A variety of such CRF analogs are well known in the art and can be used in accordance with the embodiments, see, e.g., U.S. Pat. Nos. 4,594,329; 5,112,809; 5,132,111; 5,235,036; 5,278,146; 5,439,885; 5,493,006; 7,498,300; and 7,851,588, each incorporated herein by reference in its entirety. One specific example of a CRF analog is Stressin$_1$-A (available from Tocris Bioscience, see e.g., Rivier et al., 2008), a potent and selective CRF$_1$ receptor agonist (Ki values are 1.5 and 224 nM for CRF$_1$ and CRF$_2$ receptors, respectively). The molecule has a peptide sequence of PPISLDLTFHLLREV-LEXARAEQLAQQEHSKRKLXEII (SEQ ID NO: 41), wherein Pro1 has an N-terminal Ac, X is Nle, Glu28 is γ-Glu, Lys31 is ε-Lys, Ile38 has a C-terminal amide, and the peptide is cyclized between Glu28 and Lys31.

Selective CRF$_2$ Receptor Agonists

Certain aspects of the embodiments concern selective CRF$_2$ receptor agonists. Examples of such selective CRF$_2$ receptor agonists are Urocortin 3 (Ucn 3; see, e.g., U.S. Pat. Nos. 6,953,838 and 7,459,427, incorporated herein by reference) and Urocortin 2 (Ucn 2; see, e.g., U.S. Pat. Nos. 6,838,274; 7,223,846; and 7,638,607, incorporated herein by reference). For example, a Ucn 2 or Ucn 3 polypeptide can be a human or non-human Ucn 2 or Ucn 3 or a chimera of such polypeptides, see, e.g., FIG. 3, which provides an alignment of human and non-human Ucn 2 and Ucn 3 polypeptides. The sequences of fully processed forms of these Ucn 3 polypeptides are provided as SEQ ID NOs: 21-24, and fully processed Ucn 2 polypeptides are provided as SEQ ID NOs: 25-28.

In some aspects, for example, a polypeptide with CRF$_2$ agonist activity can comprise an amino acid sequence at least about 70%, 75%, 80%, 85%, 90%, 95%, 98%, 99%, or more identical to one of the mature Urocortin polypeptides of SEQ ID NOs: 21-28. In certain aspects, the polypeptide comprises, 1, 2, 3, 4, 5, 6, 7, 8, 9, or 10 amino acid deletions, insertions, or substitutions relative the molecules of SEQ ID NOs: 21-28. For example, the polypeptide can comprise the sequence of human Ucn 3 (SEQ ID NO: 21) or human Ucn 2 (SEQ ID NO: 25) wherein 1, 2, 3, 4, 5, 6, 7, 8, 9, or 10 amino acids have been substituted for an amino acid at a corresponding position in a different Ucn 3 or Ucn 2 polypeptide or for an amino acid with a similar hydrophobic index. In still further aspects a polypeptide can be modified to enhance agonism of (or binding to) a CRF$_2$ receptor or to enhance the solubility or stability of the molecule (e.g., in vivo stability). For instance, 1, 2, 3, 4, 5, 6, 7, 8, 9, or 10 amino acids of a human or non-human Ucn 2 or Ucn 3 polypeptide can be substituted for a non-natural or rare amino acid, such as one of those shown in Table 1 below. In still further aspects, the polypeptide can be cyclized, for example by the addition of a lactam bridge in the polypeptide (e.g., in the C-terminal half of the polypeptide). In yet further aspects, a polypeptide can be conjugated, such as by PEGylation, to enhance its stability or solubility.

Methods for identifying further agonists of CRF$_2$ receptors are provided, for example, in U.S. Pat. No. 7,869,958, incorporated herein by reference.

Modification of CRF Receptor Agonist

As detailed above, in certain aspects, a CRF$_1$ receptor agonist and/or a CRF$_2$ receptor agonist are polypeptide agonists related to CRF-family members (e.g., CRF, Ucn 1, Ucn 2, or Ucn 3). CRF family members may comprise amino acid deletions, amino acid insertions, amino acid substitutions, and/or chemical changes, such as the insertion of lactam bridges, acetylation of amino acid side chains, or addition of PEG to the polypeptide. In general, modification are made to accomplish one or more of the following: to alter CRF receptor activation by the molecule, to enhance CRF receptor binding or selectivity of the molecule, or to modify the pharmacokinetics of the molecule. Thus, it will be understood that while any CRF family member can be modified in order to generate a CRF receptor agonist, CRF family members with high affinity for CRF$_1$ receptor are preferred as CRF$_1$ receptor agonists and members with high affinity for CRF$_2$ receptor are preferred as CRF$_2$ receptor agonists.

It is also contemplated that, in certain embodiments, modified CRF family members will preferentially agonize specific CRF receptor protein isoforms. For example, the affinity of modified CRF family members for the alpha, beta, and/or gamma protein isoforms of CRF$_2$ receptors can be assessed, and agonists that are specific for one or more of the isoforms can be selected. This may be of particular advantage since it is known that the expression of the various CRF receptor isoforms is variable through-out the body and thus, by targeting specific receptor isoforms, organs or tissues expressing that isoform (e.g., a cell in the pancreas) may be more specifically targeted. Again, this kind of specific receptor isoform targeting can both increase the efficacy and decrease potential side effects of agonists.

It is well known in the art that amino-terminal deletions of CRF family members can result in polypeptides that have antagonist activity, for example, see River et al., 2002, Rijkers et al., 2004, and U.S. Pat. Nos. 6,323,312; 5,874,227; 5,777,073; 5,510,458; 5,245,009; and 5,109,111. Thus in certain embodiments, modified CRF polypeptides will not comprise such deletions of amino-terminal amino acid sequences.

In certain aspects, CRF receptor agonists can be further modified by amino substitutions, for example by substituting an amino acid at one or more position with an amino acid having a similar hydrophilicity. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitutions can be made in CRF receptor agonists and will likely only have minor effects on their activity and ability to bind CRF receptors. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the polypeptide CRF receptor agonists described herein may be modified by the substitution of an amino acid, for a different, but homologous amino acid with a similar hydrophilicity value. Amino acids with hydrophilicities within +/−1.0 or +/−0.5 points are considered homologous.

It will also be understood that certain amino acids have specific properties, and thus any amino acid substitution will abolish said property. For example cysteine residues have the unique ability to form di-sulfide bonds, which can be crucial for protein structure and activity. Thus, a substitution of cysteine residue for any other amino acid may be expected, by one of skill in the art, to alter the activity of a protein. Additionally, certain CRF receptor agonists comprise a lactam bridge that structurally constrains the polypeptide. Such lactam bridges can be formed between Glu and Lys residues in a protein, and thus in certain cases amino acids may be substituted for a Glu or a Lys in order to facilitate the insertion of a lactam bridge. Such lactam bridges have been shown to be very effective in the generation of CRF receptor-binding peptides as described in Rivier et al., 2002. Therefore, in certain embodiments specific amino acids may be substituted for unlike amino acids in order to facilitate the insertion of an amino acid with a desired chemical or structural property, such as a lactam bridge.

Thus, in further aspects of the invention, modified CRF receptor-binding polypeptides can comprise one or more modified or unusual amino acid, such as those listed in Table 1. For example norleucine, a non-templated amino acid that is formed by deamination of lysine, may be substituted at one or more positions. In certain cases polypeptides of the embodiments may incorporate amino acids of the "D" chirality that do not naturally occur in proteins, and are thereby resistant to degradation. In each case such an amino acid is indicated by the letter "D" preceding the three letter abbreviation of the amino acid. For example, D-Phenylalanine is indicated by DPhe. As discussed above polypeptides according to the invention may also be cyclic, for example Glu and Lys residues may be linked by a lactam bridge (see Rijkers et al., 2004; Rivier et al., 2002).

the invention may comprise a dibenzyl oxy carboxyl group or an acetylated residue at the amino terminus. Thus, in some cases the —$NH_2$ terminus is replaced with —NH—CO—$CH_2$. In certain cases, a modified peptide or polypeptide may additionally or independently comprise an amidated (e.g., the —COOH group is replaced by —CO—$NH_2$) or esterified carboxy-terminal residue. Thus, in some highly preferred aspects, a peptide or polypeptide will comprise both an amino-terminal acetylated residue and a carboxy-terminal amidated residue. For instance, a modified CRF receptor-binding polypeptide can be amidated at the carboxy terminus, as is the case in naturally occurring, mature CRF family member polypeptides.

One of skill in the art will recognize that CRF receptor-binding polypeptides can be produced by any of the methods that are well know to those of skill in the art. For example, in certain cases the polypeptide can be expressed and purified from bacterial or insect cells. However, in certain embodiments the polypeptide can be chemically synthesized. This process in particular, readily allows the substitution of unnatural and chemically modified amino acids at any given position of the CRF receptor-binding polypeptide.

CRF Receptor-Binding Antibodies and Aptamers

In certain aspects of the embodiments CRF receptor agonists comprise antibodies that bind to and activate $CRF_1$ receptors and/or $CRF_2$ receptors. Such antibodies may comprise polyclonal and/or monoclonal antibodies or fragments thereof. Methods for generating antibodies are well known to those of skill in the art. Briefly, antibodies are raised against

TABLE 1

Modified and Unusual Amino Acids

| Abbr. | Amino Acid | Abbr. | Amino Acid |
| --- | --- | --- | --- |
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | Lys(Ac) | Acetylated-lysine |
| Baib | 3-Aminoisobutyric acid | MeGly | N-Methylglycine, sarcosine |
| Apm | 2-Aminopimelic acid | MeIle | N-Methylisoleucine |
| CαMeLeu | alpha-methyl leucine | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

It will also be understood that modified CRF receptor-binding polypeptides may include additional residues, such as additional N- and/or C-terminal amino acids and yet still be essentially as set forth in one of the sequences disclosed herein. In certain cases, for example, modified CRF polypeptides may comprise additional N- and/or C-terminal amino acids that can be chemically or proteolytically cleaved from the polypeptide. It will be understood that peptides or polypeptides will typically comprise a free amino group at the amino terminus and a free carboxy group at the carboxy terminus. However, since these groups remain reactive in a variety of chemistries it is often preferred that the amino terminus, the carboxy terminus, or both termini of a peptide or polypeptide be blocked or protected by addition of a less reactive group. For example, the amino terminus of a CRF receptor-binding polypeptide may be blocked by an acyl group. In some embodiments, a peptide and/or polypeptide of an antigen that comprises at least a portion of the $CRF_1$ receptor or $CRF_2$ receptor amino acid sequence. Thus it will be understood that antibodies can be raised against the complete CRF receptor amino acid sequence or portions thereof. As detailed below CRF receptor-derived amino acid sequence may be further coupled to additional amino acid sequences to increase its antigenicity.

Not all antibodies that bind to a CRF receptor will act as agonists, thus a CRF receptor-binding antibody can be tested for it ability to agonize the receptor. For example, CRF receptor-binding antibodies can be tested for their ability to enhance insulin section in cultured islets, similar to the studies shown in FIG. 1, or for their ability to increase beta cell mass in a mouse model, such as in Example 2 and FIG. 5.

In certain aspects of the embodiments CRF receptor-binding antibodies may be modified to enhance their efficacy as therapeutics. For example, it is preferred that polypeptide therapeutics not illicit an immune response. Thus, in the case where the subject for treatment is a human, antibodies may be human antibodies or humanized antibodies, so as to reduce the possibility of immune response. In yet further embodiments, the antibodies may be single chain antibodies since the manufacture of single chain antibodies can be substantially stream-lined by production in insect or bacterial expression systems.

It is additionally contemplated that nucleic acid aptamers that bind to CRF receptors may be used to agonize receptors. Methods for selecting aptamers by using recombinant CRF receptors or fragments thereof to purify nucleic acid aptamers from a library are well known in the art. The technique, known as SELEX, can also be automated to enhance the speed and efficacy of selection, for example, see U.S. Pat. Nos. 6,569,620 and 6,716,580. Aptamers identified to bind to a CRF receptor can then be screened for the ability to agonize the receptor, for example by the methods described herein. Methods for synthesizing and purifying nucleic acids, such as CRF receptor-binding aptamers, are well known to those of skill in the art. For example, DNA aptamers may be synthesized by PCR, while RNA aptamers can be generated by in vitro transcription. In preferred embodiments large scale preparation of aptamers may be accomplished by chemical synthesis, this method allows for the incorporation of DNA, RNA, and chemically modified oligonucleotides into to the specific aptamer sequence.

III. Therapeutic Compositions and Methods

Pharmaceutical compositions of the present invention comprise, in some instances, an effective amount of a $CRF_1$ receptor agonist and/or a $CRF_1$ receptor agonist in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains a CRF receptor agonist or additional active ingredients will be known to those of skill in the art in light of the present disclosure, as exemplified by Remington's Pharmaceutical Sciences, $18^{th}$ Ed., 1990, incorporated herein by reference. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, targeting agents (e.g., CNS targeting agents), lubricants, sweetening agents, flavoring agents, gels (e.g., gelatin), dyes, such like materials, and combinations thereof, as would be known to one of ordinary skill in the art (see, for example, Remington's Pharmaceutical Sciences, $18^{th}$ Ed., 1990, incorporated herein by reference). Except insofar as any conventional carrier is incompatible with the active ingredient, its use in the therapeutic or pharmaceutical compositions is contemplated.

A therapeutic composition of the invention may comprise different types of carriers depending on whether it is to be administered in solid, liquid, or aerosol form, and whether it needs to be sterile. The present invention can be administered intravenously, intradermally, intraarterially, intraperitoneally, intracranially, mucosally, intraocularally, subcutaneously, or intranasally, intravitreally, intravaginally, intrarectally, topically, intrathecally, intracerebroventricularly, orally, locally (e.g., into pancreatic tissue), via inhalation, via a lavage, in cremes, in lipid compositions (e.g., liposomes), or by other methods or any combination of the forgoing as would be known to one of ordinary skill in the art (see, for example, Remington's Pharmaceutical Sciences, $18^{th}$ Ed., 1990, incorporated herein by reference).

The composition may comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal, or combinations thereof. In the case of proteinacious compositions of the invention, it may also be preferable that the action of proteases be inhibited during storage of compositions. This can be accomplished by the additional of protease inhibitors and/or the storage of the compositions at low temperature prior to administration.

In embodiments where compositions according to the invention are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers, such as, for example, liquid polyol or lipids; by the use of surfactants, such as, for example, hydroxypropylcellulose; or combinations thereof such methods. In many cases, it will be preferable to include isotonic agents, such as, for example, sugars, sodium chloride, or combinations thereof.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin, or combinations thereof; an excipient, such as, for example, dicalcium phosphate, mannitol, lactose, starch, magnesium stearate, sodium saccharine, cellulose, magnesium carbonate, or combinations thereof; a disintegrating agent, such as, for example, corn starch, potato starch, alginic acid, or combinations thereof; a lubricant, such as, for example, magnesium stearate; a sweetening agent, such as, for example, sucrose, lactose, saccharin, or combinations thereof; a flavoring agent, such as, for example, peppermint, oil of wintergreen, cherry flavoring, orange flavoring, etc.; or combinations thereof the foregoing. When the dosage unit form is a capsule, it may contain, in addition to materials of the above type, carriers, such as a liquid carrier. Various other materials may be present as coatings or to otherwise modify the physical form of the dosage unit. For instance, tablets, pills, or capsules may be coated with shellac, sugar, or both.

Additional formulations that are suitable for other modes of administration include suppositories. Suppositories are solid dosage forms of various weights and shapes, usually medicated, for insertion into the rectum, vagina, or urethra. After insertion, suppositories soften, melt, or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

A. Dosages

CRF receptor agonists of the embodiments will generally be used in an amount effective to achieve the intended purpose (e.g., increased glucose-responsive insulin secretion or to increase beta cell mass). A therapeutically effective amount is an amount effective to ameliorate or prevent the symptoms (e.g., excess blood sugar), onset, or progression of clinical disease in the subject being treated. Determination of a therapeutically effective amount is well within the capabilities of those skilled in the art, especially in light of the detailed disclosure provided herein. For example, as described supra, in certain instances an effective amount of a $CRF_1$ receptor agonist and a $CRF_2$ receptor agonist of the embodiments may be defined by the ability of the compound to increase serum insulin levels or beta cell mass.

For systemic administration, a therapeutically effective dose can be estimated initially from in vitro assays. For example, a dose can be formulated in an in vitro islet culture system as described herein. Such information can be used to more accurately determine useful doses in humans.

Initial dosages can also be estimated from in vivo data, e.g., diabetic animal models, using techniques that are well known in the art and the specific techniques described herein. One having ordinary skill in the art could readily optimize administration to humans based on animal data.

Methods for estimating dose conversions between animal models and humans have previously been developed. In general these algorithms have been used to extrapolate an animal dose to a dose that would be tolerated by a human. For example, methods for dose conversion have previously been disclosed by Freireich et al. (1966). The conversion methods taught by Freireich calculate equivalent doses between species using surface area ($m^2$) rather than mass (kg), a method that correlates much more closely to actual data than body mass conversions. Specifically, Freireich teaches how to use an animal 10% lethal dosage ($LD_{10}$) value to estimate the maximum tolerated doses in a human. Freireich also discussed method for converting a dose in mg/kg to a dose in $mg/m^2$ by using the "km" conversion factor for the given animal. For example, in the case of a laboratory mouse the km is approximately 3.0. Thus, in mice $mg/m^2$=km (3.0 for mice)×dose in mg/kg.

More recent studies regarding species dose scaling have further elaborated upon the methods of Freireich. These newer studies have reduced error associated with conversion between species to determine human tolerable doses. For example, Watanabe et al. (1992) describes that a conversion of doses between species using body surface area may not be the most accurate method per se for predicting a human equivalent dosage. Nonetheless, the scaling factors set forth by Watanabe yield results that are with-in the margin of error of the older Freireich conversions. Currently accepted methods for determining a proper starting dose in humans expand upon the methods set forth by Freireich. For example, Mahmood et al. (2003) provides a discussion regarding the choice of a proper starting dose in humans given dose studies in animals.

The actual dosage amount of a composition of the present invention administered to a subject can be determined by physical and physiological factors, such as body weight, severity of condition, the type of disease being treated, previous or concurrent therapeutic interventions, idiopathy of the patient, and the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

An effective amount of the therapeutic composition is determined based on the intended goal. The term "unit dose" or "dosage" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the protection desired. Thus, in some cases dosages can be determined by measuring, for example, changes in serum insulin or glucose levels of a subject.

Precise amounts of the therapeutic composition may also depend on the judgment of the practitioner and are peculiar to each individual. The amount of a molecule administered will, of course, be dependent on the subject being treated, on the subject's weight, the severity of the affliction, the manner of administration, and the judgment of the prescribing physician. Other factors affecting the dose include the physical and clinical state of the patient, the route of administration, the intended goal of treatment (e.g., alleviation of symptoms versus attaining a particular serum insulin or glucose concentration), and the potency, stability, and toxicity of the particular therapeutic substance. The therapy may be repeated intermittently while symptoms are detectable or even when they are not detectable.

B. Toxicity

Preferably, a therapeutically effective dose of a CRF receptor agonist(s) described herein will provide therapeutic benefit without causing substantial toxicity.

Toxicity of the molecules described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins that exhibit high therapeutic indices are preferred. The data obtained from these cell culture assays and animal studies can be used in formulating a dosage range that is not toxic for use in humans. The dosage of the proteins described herein lies preferably within a range of circulating concentrations that include the effective dose with little or no toxicity. The dosage may vary within this range depending upon the dosage form employed and the route of administration utilized. The exact formulation, route of administration, and dosage can be chosen by the individual physician in view of the patient's condition. (See, e.g., Fingl et al., 1975).

C. Combination Therapies

A variety of conventional pharmacological treatments for diabetes are in the art (see, e.g., Florence and Yeager, 1999) and may be used in combination with the methods of the embodiments. In some aspects of the invention, one or more of these agents may be administered in combination or in conjunction with compositions according the invention. Such combination therapy may reduce the effective dosage of currently available drugs and thus reduce the side effects associated with therapy regimens. Some specific compounds currently in use comprise: insulin; sulfonylureas, such as tolbutamide (Orinase®) and chlorpropamide; biguanides, such as metformin; alpha-glucosidase inhibitors, such as acarbose and miglitol; thiazolidinediones, such as rosiglitazone, pioglitazone, and troglitazone; and repaglinide.

Treatment with CRF receptor agonists according to the embodiments may precede or follow an anti-diabetes therapy by intervals ranging from minutes to weeks. In embodiments where the CRF receptor agonist therapy and secondary therapy are applied separately to a cell or patient, one would generally ensure that a significant period of time did not expire between the time of each delivery, such that the CRF receptor therapy and secondary therapy would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly where several days (e.g., 2, 3, 4, 5, 6, or 7 days) to several weeks (e.g., 1, 2, 3, 4, 5, 6, 7, or 8 weeks) lapse between the respective administrations.

Various combinations may be employed, where the $CRF_1$ receptor agonist and $CRF_2$ receptor agonist therapy is "A" and the secondary agent, such as an anti-diabetes therapy, is "B":

| A/B/A | B/A/B | B/B/A | A/A/B | A/B/B | B/A/A |
|---|---|---|---|---|---|
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Under certain conditions insulin treatment may be used in conjunction with the methods according to the instant invention.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

$CRF_1$ and $CRF_2$ Receptor Agonists Synergistically Stimulate Islet Cell Insulin Secretion Human islets were handpicked twice and cultured overnight in CMRL-1066 medium (Invitrogen™) supplemented with 10% fetal bovine serum (FBS) and penicillin/streptomycin at 37° C., 5% $CO_2$. Islets were starved in RPMI 1640 medium supplemented with 1.4 mM glucose and 0.1% BSA for 60 min and then were transferred into 1.2 mL of medium (RPMI 1640 supplemented with 2.8 mM glucose, 0.1% BSA) in 24-well plates at 100 islets/well. After 60 min, 600 µL of medium was collected for the determination of basal insulin release, and then islets were stimulated for 60 min with glucose and peptide as indicated in RPMI 1640 containing 0.1% BSA. Samples were diluted 20 times in RPMI 1640 with 0.1% BSA and were stored at −20° C. until determination of insulin concentrations with an insulin ELISA kit (Mercodia AB).

Peptides used in the studies were ovine CRF (oCRF), a selective CRF-R1 agonist; human Urocortin 3 (hUcn 3), a selective CRF-R2 agonist; antalarmin, a selective CRF-R1 antagonist; and astressin$_2$-B, a selective CRF-R2 antagonist. The studies demonstrate that the islets cells secrete a moderate amount of insulin upon an increase in glucose concentration. Insulin secretion was enhanced by addition of either a $CRF_1$ receptor agonist (oCRF) or a $CRF_2$ receptor agonist (hUcn 3). Surprisingly, however, when an agonist of both $CRF_1$ and $CRF_2$ receptors were applied to the cells insulin secretion was synergistically enhanced. The synergistic enhancement was inhibited by the addition of either a $CRF_1$ receptor antagonist (antalarmin) or a $CRF_2$ receptor antagonist (astressin$_2$-B) to the cells (FIG. 1).

Example 2

Ucn1 Expression Increases Pancreatic Beta Cell Mass

Figure 5:
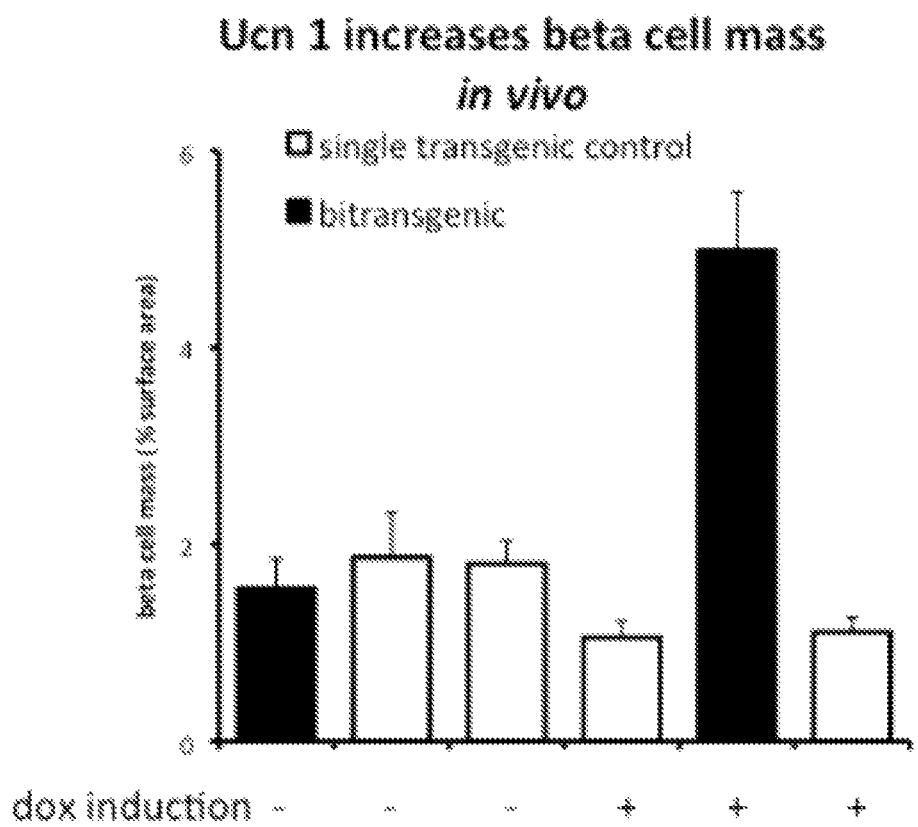
FIG. 5: Ucn1 expression increases beta cell mass. Single transgenic (control) or bitransgenic mice were generated as detailed in Example 2, such that Ucn1 expression is induced only in the pancreas of bitransgenic mice in the presence of doxycycline (dox). The indicated animals were treated with or without dox from 21 days to 9 weeks of age and total beta cell mass (as a proportion of pancreatic mass) was calculated by immunostain and plotted. Bars indicate the average beta cell area across six sections per animal; error bars indicate the standard errors.

A transgenic mouse model that features beta cell-specific, doxycycline-inducible expression of Ucn 1 was generated by routine transgenic techniques. Single transgenic mice were obtained comprising either an expressible tetracycline transactivator (tTA) protein under the control of a pancreas-specific Insulin2 promoter (Jax Stock#008250 STOCK Tg(Ins2-rtTA)2Efr/J) or expressible Ucn1 under the control of a tTA protein-activated promoter (see, e.g., Sun et al., 2007 and Mallo, 2006). Single transgenic mice were crossed to generate the bitransgenic mice referenced in the studies. Thus, transgenic Ucn 1 expression in beta cells requires the presence of two transgenic cassettes as well as the administration of doxycycline. According to this arrangement, single transgenic animals or bitransgenic animals that do not receive doxycycline do not express transgenic Ucn 1. Bitransgenic animals, along with single transgenic controls, were administered doxycyline continuously as indicated from 21 days until 9 weeks of age. The entire pancreas was collected from each animal and fixed in 4% paraformaldehyde, followed by sucrose protection (30% sucrose). Tissues were embedded and sectioned to 14 micron thickness and mounted on coated microscope slides. Six sections per animal were stained with a 1:500 dilution of a guinea pig anti-insulin antiserum (Dako) in KPBS with 2% normal donkey serum and 0.4% Triton X-100 overnight at 4° C. Donkey anti-guinea pig-Cy3 was used as a secondary antibody at a 1:600 dilution. Sections were mounted in fluorescence mounting media containing dapi counterstain. Each section was scanned and the total pancreas surface area (based on the dapi counterstain) and the total beta cell surface area (based on the insulin-Cy3 stain) were quantified using standard morphometry techniques using Metamorph software. Beta cell area in each animal was expressed as the insulin+ surface area as a percentage of the total surface area (FIG. 5). Doxycycline administration for 6 weeks to a bitransgenic animal (FIG. 5, closed bar) led to a robust increase in beta cell mass compared to single transgenic controls on doxycycline or a bitransgenic animal that did not receive doxycycline.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,594,329
U.S. Pat. No. 5,109,111
U.S. Pat. No. 5,112,809
U.S. Pat. No. 5,132,111
U.S. Pat. No. 5,235,036
U.S. Pat. No. 5,245,009
U.S. Pat. No. 5,278,146
U.S. Pat. No. 5,439,885
U.S. Pat. No. 5,493,006
U.S. Pat. No. 5,510,458
U.S. Pat. No. 5,777,073
U.S. Pat. No. 5,874,227
U.S. Pat. No. 6,214,797
U.S. Pat. No. 6,323,312
U.S. Pat. No. 6,569,620
U.S. Pat. No. 6,716,580
U.S. Pat. No. 6,838,274
U.S. Pat. No. 6,953,838
U.S. Pat. No. 7,223,846
U.S. Pat. No. 7,459,427
U.S. Pat. No. 7,498,300
U.S. Pat. No. 7,638,607
U.S. Pat. No. 7,851,588
U.S. Pat. No. 7,869,958
Fingl et al., In: *The Pharmacological Basis of Therapeutics*, 1:1, 1975.
Florence and Yeager, *Amer. Fam. Phys.*, 59(10):2835-2844, 2849-2850, 1999.
Freireich et al., *Cancer Chemother. Reports*, 50:219-244, 1966.
Kyte and Doolittle, *J. Mol. Biol.*, 157(1):105-132, 1982.
Mahmood et al., *J. Clin. Pharmacol.*, 43:692-697, 2003.
Mallo, *Front Biosci.*, 11:313-327, 2006.
Remington's Pharmaceutical Sciences, 18th Ed. Mack Printing Company, 1289-1329, 1990.
Rijkers et al., *Bioorg. Med. Chem.*, 12(19):5099-5106, 2004.
Rivier et al., *J. Med. Chem.*, 45:4737-4747, 2002.
Rivier et al., *J. Med. Chem.*, 50:1668-1674, 2008.
Sun et al., *Acta Biochim Biophys Sin* (Shanghai) 39:235-246, 2007.
Watanabe et al. *Risk Analysis*, 12:301-310, 1992.

What is claimed is:

1. A method for stimulating insulin secretion and increasing beta cell mass in a diabetic subject comprising, administering a Urocortin 1 polypeptide to the subject in an amount effective to stimulate insulin secretion and increase beta cell mass in the subject.

2. The method of claim 1, wherein the subject is human.

3. The method of claim 1, wherein the subject has been diagnosed with type II diabetes.

4. The method of claim 1, wherein the Urocortin 1 polypeptide is formulated in a pharmaceutical composition.

5. The method of claim 1, wherein the Urocortin 1 polypeptide is administered intravenously, intradermally, intraarterially, intraperitoneally, subcutaneously, or intramuscularly.

6. The method of claim 1, wherein the subject has been diagnosed with type I diabetes.

7. The method of claim 1, wherein the Urocortin 1 polypeptide is delivered selectively to pancreatic tissues.

8. The method of claim 7, wherein the Urocortin 1 polypeptide is administered locally to pancreatic tissues.

* * * * *